United States Patent
Hutchins et al.

(10) Patent No.: US 6,720,156 B2
(45) Date of Patent: Apr. 13, 2004

(54) SUPERFICIAL ZONE PROTEIN-BINDING MOLECULES AND USES THEREOF

(75) Inventors: Jeff T. Hutchins, Chapel Hill, NC (US); Klaus E. Kuettner, Chicago, IL (US); Kathryn Mason Lindley, Chapel Hill, NC (US); Thomas M. Schmid, Downers Grove, IL (US); Barbara L. Schumacher, Cardiff by the Sea, CA (US); Stephen Anthony Stimpson, Chapel Hill, NC (US); Jui-Lan Su, Chapel Hill, NC (US)

(73) Assignees: SmithKline Beecham Corporation, Philadelphia, PA (US); Rush-Presbyterian St Luke's Medical Center, Chicago, IL (US)

( * ) Notice: Subject to any disclaimer, the term of this patent is extended or adjusted under 35 U.S.C. 154(b) by 236 days.

(21) Appl. No.: 09/780,718

(22) Filed: Feb. 9, 2001

(65) Prior Publication Data

US 2002/0009761 A1 Jan. 24, 2002

Related U.S. Application Data

(60) Provisional application No. 60/181,377, filed on Feb. 9, 2000, and provisional application No. 60/201,989, filed on May 3, 2000.

(30) Foreign Application Priority Data

Feb. 10, 2000 (GB) .............................................. 0003092

(51) Int. Cl.$^7$ .............................................. G01N 33/53
(52) U.S. Cl. ...................... 435/7.1; 435/7.92; 435/7.93; 435/7.94; 435/329; 435/344.1; 436/547; 436/86
(58) Field of Search ................................. 435/7.1, 7.92, 435/7.93, 7.94, 329, 344.1; 436/547, 86

(56) References Cited

FOREIGN PATENT DOCUMENTS

WO    WO 98/08949    3/1998
WO    WO 00/64930    11/2000

OTHER PUBLICATIONS

Borrebaeck eds. Antibody Engineering, A practical guide, Ch 5, W.H. Freeman and Company (1992).*
Alini et al., "In serum–free culture thyroid hormones can induce full expression of chondrocyte hypertrophy leading to matrix calcification," *Journal of Bone and Mineral Research* 11(1):105–113 (1996).
Ikegawa et al., "Isolation, characterization and mapping of the mouse and human PRG4 (proteoglycan 4) genes," *Cytogenetics and Cell Genetics* 90(3/4):291–297 (2000).
Jay et al., "Lubricin is a product of megakaryocyte stimulating factor gene expression by human synovial fibroblasts," *The Journal of Rheumatology* 27(3):594–600 (Mar. 2000).
Jay et al., "Homology of lubricin and superficial zone protein (SZP): products of megakaryocte stimulating factor (MSF) gene expression by human synovial fibroblasts and articular chondrocytes localized to chromosome 1q25," *Journal of Ortopaedic Research* 19(4):677–687 (Jun. 2001).

Robbins et al., "Immortalized human adult articular chondrocytes maintain cartilage–specific phenotype and responses to interleukin–1 beta," *Arthritis & Rheumatism* 43(10):2189–2201 (Oct. 2000).
Theiler et al., "Clinical, biochemical and imaging methods of assessing osteoarthritis and clinical trials with agents claiming 'chondromodulating' activity," *Osteoarthritis and Cartilage* 2(1):1–23 (Mar. 1994).
Aydelotte, M.B. and Kuettner, K.E. "Differences between sub–populations of cultured bovine articular chondrocytes. I. Morphology and cartilage matrix production," *Connect Tissue Res.* 18:205–222 (1988).
Aydelott, M.B. and Juettner, K.E. "Differences between sub–populations of cultured bovine articular chondrocytes. II. Proteoglycan metabolism." *Connect Tissue Res.* 18:223–234 (1988).
Flannery, C.R. et al. "Articular cartilage superficial zone protein (SZP) is homologous to megakaryocyte stimulating factor precursor and is a multifunctional proteoglycan with potential growth–promoting, cytoprotective, and lubricating properties in cartilage metabolism." *Biochem. Biophys. Res. Commun.* 254(3):535–541 (1999).
Kilpatrick, K.E. et al. "Rapid development of affinity matured monoclonal antibodies using RIMMS," *Hybridoma* 16(4):381–389 (1997).
Lindley, K.M. et al. "Production of monoclonal antibodies using recombinant baculovirus displaying gp64–fusion proteins," *J. Immun. Methods* 234:123–135 (2000).
Marcelino, J. et al. "CACP, encoding a secreted proteoglycan, is mutated in camptodactyl–arthropathy–coxa vara–pericarditis syndrome," *Nature Genetics* 23:319–322.
Merberg et al. A Comparison of Vitronectin and Megakaryocyte Stimulaing Factor. In: Biology of Vitronectins and their Receptors (eds. Pressner et al.) pp. 45–53 (1993).
Schmid, T.M. et al. "Immunohistochemical distribution of a novel proteoglycan in the surface lamina of articular cartilage," *Proceedings of the Orthopedic Res. Soc.* p. 97–117 (1994).

(List continued on next page.)

*Primary Examiner*—Long V. Le
*Assistant Examiner*—Changhwa J. Cheu
(74) *Attorney, Agent, or Firm*—Michael M. Conger

(57) ABSTRACT

The invention provides an antibody or a fragment thereof having specific binding affinity for superficial zone protein (SZP) or a variant, fragment, or protein core thereof, wherein the binding affinity of the antibody or fragment thereof for human superficial zone protein is the same or greater than the binding affinity for bovine superficial zone protein in a competitive binding assay, IAsys analysis, or BIAcore analysis. The present invention further provides hybidoma cells that produce the monoclonal antibody and antibody reagent kits comprising the antibody or fragment of the invention. Further provided by the invention are methods of SZP detection, methods of diagnosing a degenerative joint condition, and screening methods related to the use of the antibody or fragment thereof.

10 Claims, 3 Drawing Sheets

OTHER PUBLICATIONS

Schumacher, B.L. et al. "Chondrocytes of the superficial zone of bovine articular cartilage synthesize and secrete a novel proteoglycan," Orthopaedic Research Society, poster presentation, 40$^{th}$ Annual Meeting, New Orleans, LA (Feb. 21–24, 1994).

Schumacher, B.L. et al. "Macromolecules synthesized by articular chondrocytes of the superficial zone but not the deeper zones are also synthesized by synovium," Orthopaedic Research Society, poster presentation, 41$^{st}$ Annual Meeting, Orlando, Florida, Feb. 13–16, 1995, *Trans. Orthop. Res. Soc.* 20:397 (1995).

Schumacher, B.L. et al. "A novel proteoglycan synthesized by superficial–zone chondrocytes of articular cartilage," American College of Rheumatology, platform presentation, *Arthr. Rheum.* 36:S90 (1993).

Schumacher, B.L. et al. "A novel proteoglycan synthesized and secreted by chondrocytes of the superficial zone of articular cartilage," *Arch. Biochem. Biophys.* 311(1):144–152 (1994)

Schumacher, B.L. et al. "Immunolocalization of a novel proteoglycan synthesized by cells lining the synovia cavity," *Trans. Orthop. Res. Soc.* 23:442 (1998).

Schumacher, B.L. et al. "Immunodetection and partial cDNA sequence of the proteoglycan, Superficial Zone Protein, synthesized by cells lining synovia joints," *J. Orthop. Res.* 17:110–120 (1999).

Su, J–L. et al. "Monoclonal antibodies against human collagenase and stromelysin," *Hybridoma* 14(4):383–390 (1995).

Tudor, D. et al. "Superficial Zone Proteoglycan Biosynthesis is Stimulated by Growth Factors But Inhibited by IL–1 In Chondrocytes Maintained in Agarose Cultures," 45$^{th}$ Annual Meeting, Orthopaedic Research Society, Anaheim, CA (Feb. 1–4, 1999).

* cited by examiner

SUPERFICIAL ZONE PROTEIN-BINDING MOLECULES AND USES THEREOF

CROSS REFERENCE TO RELATED APPLICATIONS

This application claims priority from Great Britain application number 0003092.4 filed Feb. 10, 2000. This application is a continuation in part of and claims the benefit of U.S. Provisional Application Ser. No. 60/181,377, filed Feb. 9, 2000, which status is pending and the entirety of which is incorporated herein by this reference. This application is also a continuation in part of and claims the benefit of U.S. Provisional Application Ser. No. 60/201,989, filed May 3, 2000, which status is pending and the entirety of which is incorporated herein by this reference.

ACKNOWLEDGEMENTS

This invention was made in part with government support under grant 2P50-AR39239 awarded by the National Institute for Arthritis and Musculoskeletal Diseases of the National Institutes of Health. The government has certain rights in the invention.

BACKGROUND OF THE INVENTION

1. Field of the Invention

The present invention generally relates to superficial zone protein-binding molecules and their uses, including therapeutic uses in the diagnosis, screening, and imaging in degenerative joint disease.

2. Background Art

Articular cartilage is a highly organized, heterogeneous, avascular, resilient, weight-bearing tissue that covers the ends of bones in diarthrodial (synovial) joints. The organizational arrangement of articular cartilage is marked by zonal differences. For example, the superficial zone of adult articular cartilage is distinctly different from the middle, deep, and calcified zones of the underlying cartilage in cellularity, morphology, matrix and macromolecular composition (which includes the presence of gene products made in different zones), macromolecular organization, and material properties. Among the metabolic differences is the synthesis of a proteoglycan, called superficial zone protein (SZP), which is synthesized and secreted by chondrocytes in the superficial zone of articular cartilage but is not synthesized or secreted by chondrocytes in the deeper zones of the tissue (Schumacher et al. (1994) Arch. Biochem. Biophys. 311:144–52).

SZP, which is homologous to human megakaryocyte stimulating factor precursor (MS F) and camptodactyly-arthropathy-coxa vara-pericarditis (CACP) protein, has an apparent molecular weight of 345 kDa and is substituted with keratan sulfate and chondroitin sulfate glycosaminoglycan chains (Schumacher et al. (1994) Arch. Biochem. Biophys. 311:144–52). Removal of the glycosaminoglycan side chains results in minimal change in molecular weight, which suggests that SZP has only small glycosaminoglycan chains on its core protein and that it is not an aggrecan metabolite (Schumacher et al. (1999), J. Orthop. Res 17:110–120). SZP contains large (76–78 repeats) and small (6–8 repeats) mucin-like O-linked oligosaccharide-rich repeat domains flanked by cysteine-rich N- and C-terminal domains (Flannery et al. (1999) Biochem. Biophys. Res. Comm. 254:535–541). The protein core contains potential sites for N-linked oligosaccharide and glycosaminoglycan attachment, and a putative heparin-binding domain (Id.). The heparin binding domain is encoded by exon 4 of MSF. Merberg et al. (1993) In: Biology of Vitronectins and Their Receptors (eds. Pressner et al.), pp. 45–53. Chondrocytes in the superficial zone and cells of the synovial lining, in vivo and in vitro, have been shown to synthesize SZP (Schumacher et al. (1999), J. Orthop. Res 17:110–120). Unlike other proteoglycan molecules, such as aggrecan, decorin, biglycan, and fibromodulin, very little SZP is retained in the matrix surrounding the chondrocytes (Schumacher et al. (1994) Arch. Biochem. Biophys. 311:144–52). The SZP proteoglycan present in synovial fluid has a lower molecular weight than SZP in the cartilage matrix, suggesting that either there are differences in glycosylation of SZP produced by synovial cells as compared to SZP produced by chondrocytes or that the proteoglycan is partially degraded in the synovial fluid (Schumacher et al. (1999), J. Orthop. Res 17: 110–120).

SZP forms a thin layer on the surface of adult bovine articular cartilage but not fetal articular cartilage (Schumacher et al. (1999), J. Orthop. Res 17:110–120). The thickness of the stained layer increases gradually near the junction of articular cartilage with synovium and the synovium also contains SZP (Schmid et al. (1994) Proceedings of the Orthopedic Research Society, p. 97–17.). This accumulation on adult articular cartilage has been hypothesized to be due to entrapment of SZP in an acellular collagenous layer at the surface of articular cartilage (Schumacher et al. (1999), J. Orthop. Res 17:110–120). The biosynthesis of SZP by chondrocytes has been shown to be upregulated by certain growth factors and cytokines, such as TGFβ and IGF-1, but down regulated by others, such as IL-1 (Flannery et al. (1999) Biochem Biophys. Res. Comm. 254:535–541).

SZP is thought to play a role in normal articular cartilage and in degenerative joint conditions. Recently, molecular defects in human SZP have been identified in individuals with camptodactyl-arthropathy-coxa vara-pericarditis syndrome (CACP), a very rare condition that can be marked by a proliferation of synovial cells, severe limitations in joint range of motion, and non-inflammatory pericarditis (Marcelino et al. (1999) Nature Genetics 23:319–322). Accordingly, it is desirable to detect SZP in various mammalian species, including humans, in order to monitor modulations in SZP levels, localization, and function.

SUMMARY OF THE INVENTION

In accordance with the purpose(s) of this invention, as embodied and broadly described herein, this invention, in one aspect, relates to a polyclonal or monoclonal antibody or a fragment thereof having specific binding affinity for superficial zone protein (SZP), wherein the binding affinity of the antibody or fragment thereof for human superficial zone protein is the same or greater than the binding affinity for bovine superficial zone protein in a competitive binding assay, IA sys analysis, or BIAcore analysis. Preferably the ligand is SZP or a variant, fragment, or protein core thereof. The present invention further provides a hybidoma cell that produces the monoclonal antibody of the invention. The invention also provides an antibody reagent kit comprising the antibody or fragment thereof of the invention and reagents for detecting binding of the antibody or fragment thereof to a ligand. In one embodiment, the kit further comprises containers containing the antibody or fragment thereof of the invention and containers containing the reagents.

In another aspect, the invention relates to methods of detecting SZP and methods of diagnosing degenerative conditions, such as joint, connective tissue, and blood disorders. Specifically, provided is a method of detecting superficial zone protein in a sample, comprising contacting the sample with the antibody or fragment of the present invention, under conditions in which an antigen/antibody complex can form; and detecting the presence of the antigen/antibody complex, wherein the presence of the antigen/antibody complex indicates the presence of superficial zone protein in the sample. Preferably the sample is selected from the group consisting of body fluids, such as synovial fluid, tears, saliva, urine, serum, plasma, and bone marrow, and connective tissue and components thereof, such as synovium, tendon, tendon sheath, ligament, meniscus, intervertebral disk, pericardium, chondrocytes, and articular cartilage. The method of diagnosing a degenerative joint condition in a subject, as provided by the present invention, comprises obtaining a test sample from the subject; detecting superficial zone protein in the test sample; and comparing the amount of superficial zone protein in the test sample with an amount present in a control sample; a modulated amount of superficial zone protein in the test sample indicating the degenerative joint condition.

In yet another aspect, the invention relates to screening methods, including a method of screening for a substance that modulates levels of superficial zone protein, comprising contacting a test sample with the substance to be screened, wherein the test sample contains superficial zone protein-producing cells; contacting, under conditions in which an antigen/antibody complex can form, the superficial zone protein in the test sample with the antibody or a fragment of the invention; detecting the level of the antigen/antibody complex in the test sample; and comparing the level of the antigen/antibody complex in the test sample with the level of antigen/antibody complex in a control sample; a lower or higher level of the antigen/antibody complex in the test sample indicating a substance that modulates levels of superficial zone protein. The superficial zone protein-producing cells are selected from the group consisting of chondrocytes, synovial cells, pericardial cells, and bone marrow cells of any species. Further provided is a method of screening for a substance that reduces a degenerative condition, such as a degenerative joint condition, in a subject, comprising contacting a first test sample from the subject with the antibody or fragment thereof of the invention, under conditions in which an antigen/antibody complex can form; detecting the level of the antigen/antibody complex in the first test sample; treating the subject with the substance to be screened; contacting a second test sample from the subject with the antibody or fragment of the invention, under conditions whereby an antigen/antibody complex can form; detecting the level of the antigen/antibody complex in the second test sample; and comparing the level of the antigen/antibody complex in the first test sample with the level of antigen/antibody complex in the second test sample, a modulated level of the antigen/antibody complex in the second test sample indicating a substance that reduces the degenerative condition. Alternatively, in one embodiment, the test sample is compared to a known standard or to a control sample from a second untreated subject with degenerative disease.

The invention also relates to a method of screening for subjects who would benefit from treatment for a degenerative joint condition, comprising the steps of obtaining a test sample from each subject; detecting superficial zone protein in the test samples; and comparing the amount of superficial zone protein in the test samples with an amount present in a control sample, a modulated amount of superficial zone protein in the test sample indicating a subject that would benefit from treatment for the degenerative joint condition. Also provided a method of monitoring a subject's response to a treatment for a degenerative joint condition, comprising contacting a first test sample from the subject to be monitored with the monoclonal antibody or fragment thereof of the invention, under conditions that allow formation of an antigen/antibody complex; detecting the level of the antigen/antibody complex in the first test sample; treating the subject; contacting a second test sample from the subject with the antibody or fragment thereof, under conditions whereby an antigen/antibody complex can form; detecting the level of the antigen/antibody complex in the second test sample; and comparing the level of the antigen/antibody complex in the first test sample with the level of antigen/antibody complex in the second test sample, a modulated level of the antigen/antibody complex in the second test sample indicating the subject's response to the treatment.

Further related to the invention is a method of imaging an articular surface and/or synovium of a joint, comprising contacting the articular surface and/or synovium of the joint with the antibody or fragment of the invention, under conditions in which an antigen/antibody complex can form on the articular surface and/or synovium, wherein the antibody or fragment thereof is detectably tagged; visualizing the detectable tag in antigen/antibody complexes in a plurality of locations on the articular surface; the visualization of detectable tag in antigen/antibody complexes showing the articular surface of the joint.

Additional advantages of the invention will be set forth in part in the description that follows and, in part, will be obvious from the description or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate (one) several embodiment(s) of the invention and together with the description, serve to explain the principles of the invention.

DETAILED DESCRIPTION OF THE INVENTION

Figure 1:
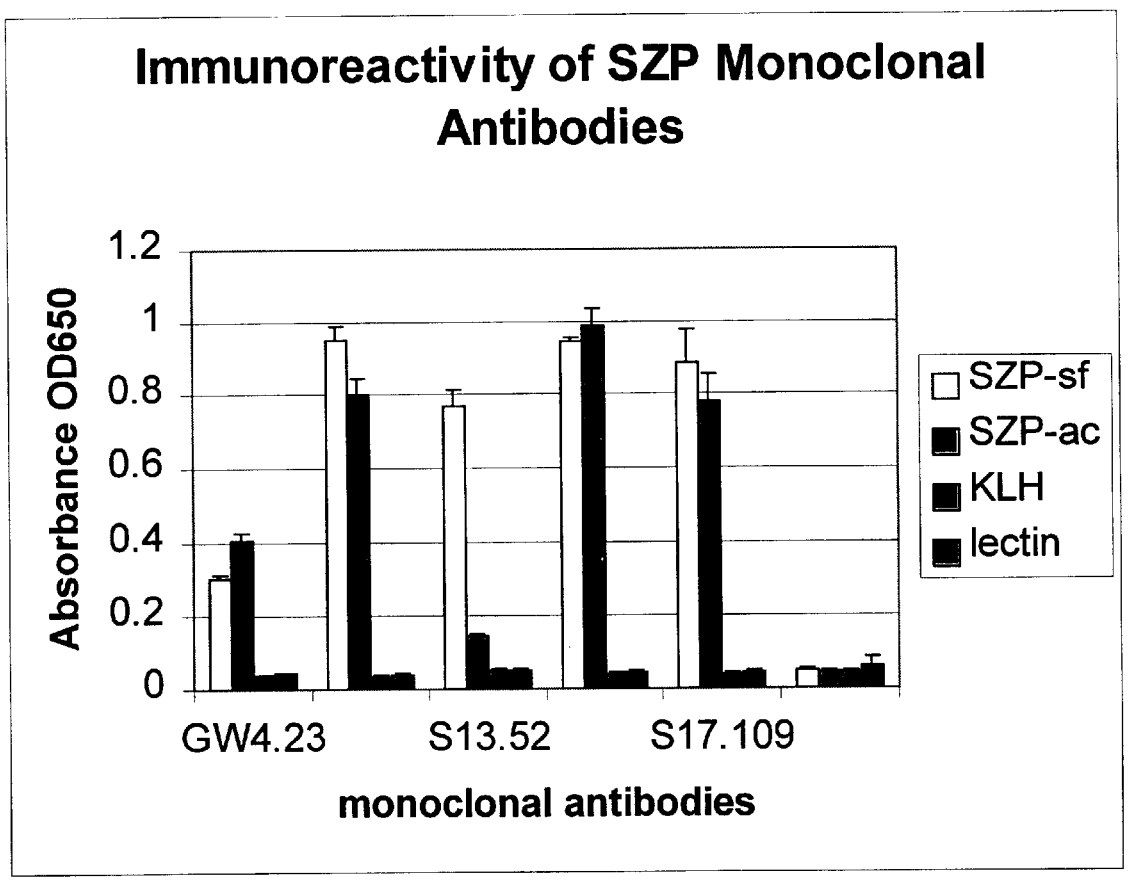
FIG. 1 shows the ELISA data using a monoclonal antibody (GW4.23) to SZP, four monoclonal antibodies (S6.79, S17.109, S13.52, S13.233) and a control monoclonal antibody to glutathione S-transferase. MAb S6.79, derived from SZP-KLH immunization, S13.233 and S17.109, derived from immunization with a mixture of SZP and hyaluronic acid (SZP-HA), show strong immunoreactivity against SZP purified from both synovial fluid (SZP-sf) and articular cartilage (SZP-ac), with no cross-reactivity against KLH or lectin. GW4.23 also shows specific but lower immunoreactivity against SZP from both preparations. S13.52, raised against synovial fluid derived-SZP-HA complex, is the only monoclonal antibody that shows differential reactivity against SZP from different sources. There was no immunoreactivity with the negative control antibody 129R10.

The present invention may be understood more readily by reference to the following detailed description of preferred embodiments of the invention and the Examples included therein and to the Figures and their previous and following description.

Before the present compounds, compositions, articles, devices, and/or methods are disclosed and described, it is to be understood that this invention is not limited to specific antibodies, specific hybridomas, or to particular methods, as such may, of course, vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Thus, for example, reference to "an antibody" includes mixtures of antibodies, reference to "a pharmaceutical carrier" includes mixtures of two or more such carriers, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not. For example, the phrase "optionally obtained prior to treatment" means obtained before treatment, after treatment, or not at all.

The invention provides an antibody (monoclonal or polyclonal) or a fragment thereof having specific binding affinity for superficial zone protein (SZP), wherein the binding affinity of the antibody or fragment thereof for human superficial protein is the same or greater than the binding affinity for bovine superficial zone protein in a competitive binding assay, IAsys analysis, or BIAcore analysis. In a preferred embodiment, the antibody is a monoclonal antibody. The antibody is raised to SZP from any species, including, for example, human, pig, guinea pig, dog, or rabbit.

Having "the same or greater" binding affinity as compared to the affinity for bovine SZP means that the antibody has less affinity for bovine than for human SZP, including, for example, when the binding for bovine SZP does not exceed background levels of binding. Thus, the antibody may have no affinity over background for bovine SZP or it may have the same affinity for bovine SZP as for human or any amount in between.

As used throughout, "superficial zone protein" or "SZP" includes the full length proteoglycan, the full length protein core, variants of SZP (e.g., alternatively spliced variants), fusion proteins comprising SZP, and immunogenic fragments of SZP, which are glycosylated or non-glycosylated SZP and which are non-reduced or reduced SZP. For example, the antibody binds full length SZP, a variant of SZP (e.g., an alternatively spliced variant), the protein core of SZP, a fusion protein, or any epitope thereon. The SZP to which the antibody is raised is naturally occurring or recombinant. The antibody can be used in techniques or procedures such as diagnostics, screening, or imaging. Anti-idiotypic antibodies and affinity matured antibodies are also considered to be part of the invention.

As used herein, the term "antibody" encompasses, but is not limited to, whole immunoglobulin (i.e., an intact antibody) of any class. Native antibodies are usually heterotetrameric glycoproteins, composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (V(H)) followed by a number of constant domains. Each light chain has a variable domain at one end (V(L)) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains. The light chains of antibodies from any vertebrate species can be assigned to one of two clearly distinct types, called kappa (k) and lambda (l), based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. The heavy chain constant domains that correspond to the different classes of immunoglobulins are called alpha, delta, epsilon, gamma, and mu, respectively.

The term "variable" is used herein to describe certain portions of the variable domains that differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a b-sheet configuration, connected by three CDRs, which form loops connecting, and in some cases forming part of, the b-sheet structure. The CDRs in each chain are held together in close proximity by the FR regions and, with the CDRs from the other chain, contribute to the formation of the antigen binding site of antibodies (see Kabat E. A. et al., "Sequences of Proteins of Immunological Interest," National Institutes of Health, Bethesda, Md. (1987)). The constant domains are not involved directly in binding an antibody to an antigen, but exhibit various effector functions, such as participation of the antibody in antibody-dependent cellular toxicity.

As used herein, the term "antibody or fragments thereof" encompasses chimeric antibodies and hybrid antibodies, with dual or multiple antigen or epitope specificities, and fragments, such as F(ab')$_2$, Fab', Fab and the like, including hybrid fragments. Thus, fragments of the antibodies that retain the ability to bind their specific antigens are provided. For example, fragments of antibodies which maintain SZP binding activity are included within the meaning of the term "antibody or fragment thereof." Such antibodies and fragments can be made by techniques known in the art and can be screened for specificity and activity according to the methods set forth in the Examples and in general methods for producing antibodies and screening antibodies for specificity and activity (See Harlow and Lane. Antibodies, A Laboratory Manual. Cold Spring Harbor Publications, New York, (1988)).

Preferably, the antibodies are derived using SZP as an immunizing agent in one of several forms, including for example, modified or non-modified SZP. "Modified" forms of SZP include, for example, superficial zone protein-keyhole limpet hemocyanin (SZP-KLH) conjugate or a mixture of SZP and hyaluronic acid (SZP-HA). A summary of examples of various monoclonal antibodies generated from various forms of SZP is provided as Table I.

two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522–525 (1986); Riechmann et al., Nature, 332:323–327 (1988); and Presta, Curr. Op. Struct. Biol., 2:593–596 (1992)).

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al., Nature, 321:522–525 (1986); Riechmann et al., Nature, 332:323–327 (1988); Verhoeyen et al., Science, 239:1534–1536 (1988)), by substituting rodent CDRs or CDR sequences for the corresponding sequences of a human antibody. Accordingly, such

TABLE 1

Summary of SZP Monoclonal Antibodies

| MAb | Antigen | Isotype | Affinity $K_D$ (M) | Immunoreactivity* | | | | | | |
|---|---|---|---|---|---|---|---|---|---|---|
| | | | | human SF | human plasma | human serum | bovine SF | dog SF | g. pig SF | rabbit SF |
| GW4.23 | SZP | IgG1 | | + | + | - | | | | |
| S6.79 | SZP-KLH | IgG2b | $3.14 \times 10^{-9}$ | +++++ | + | +/- | + | ++ | +/- | ++ |
| S13.52 | SZP-HA | IgG1 | | ++++ | ++++ | +++ | | | | |
| S13.233 | SZP-HA | IgG1 | | + | ++ | + | | | | |
| S17.109 | SZP-HA | IgG2b | $1.83 \times 10^{-8}$ | +++++ | +/- | - | | | | |

Immunoreactivity*: intensity of immuno-stained bands in Western blots
strongest ++++>++++>+++>++>+>+/- faint
SF: synovial fluid Also included within the meaning of "antibody or fragments thereof" are conjugates of antibody fragments and antigen binding proteins (single chain antibodies) as described, for example, in U.S. Pat. No. 4,704,692, the contents of which are hereby incorporated by reference.

Optionally, the antibodies are generated in other species and "humanized" for administration in humans. Humanized forms of non-human (e.g., murine) antibodies are chimeric immunoglobulins, immunoglobulin chains or fragments thereof (such as Fv, Fab, Fab', F(ab')$_2$, or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues that are found neither in the recipient antibody nor in the imported CDR or framework sequences. In general, the humanized antibody will comprise substantially all of at least one, and typically "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important in order to reduce antigenicity. According to the "best-fit" method, the sequence of the variable domain of a rodent antibody is screened against the entire library of known human variable domain sequences. The human sequence which is closest to that of the rodent is then accepted as the human framework (FR) for the humanized antibody (Sims et al., J. Immunol., 151:2296 (1993) and Chothia et al., J. Mol. Biol., 196:901 (1987)). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding (see, WO 94/04679, published Mar. 3, 1994).

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region (J(H)) gene in chimeric and germ-line mutant mice results in complete inhibition of endogenous antibody production. Transfer of the human germ-line immunoglobulin gene array in such germ-line mutant mice will result in the production of human antibodies upon antigen challenge (see, e.g., Jakobovits et al., Proc. Natl. Acad. Sci. USA, 90:2551–255 (1993); Jakobovits et al., Nature, 362:255–258 (1993); Bruggemann et al., Year in Immuno., 7:33 (1993)). Human antibodies can also be produced in phage display libraries (Hoogenboom et al., J. Mol. Biol., 227:381 (1991); Marks et al., J. Mol. Biol., 222:581 (1991)). The techniques of Cote et al. and Boerner et al. are also available for the preparation of human monoclonal antibodies (Cole et al., Monoclonal Antibodies and Cancer Therapy, Alan R. Liss, p. 77 (1985); Boemer et al., J. Immunol., 147(l):86–95 (1991)).

The present invention further provides a hybidoma cell that produces the monoclonal antibody of the invention. The term "monoclonal antibody" as used herein refers to an antibody obtained from a substantially homogeneous population of antibodies, i.e., the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired activity (See, U.S. Pat. No. 4,816,567 and Morrison et al., Proc. Natl. Acad. Sci. USA, 81:6851–6855 (1984)).

Monoclonal antibodies of the invention may be prepared using hybridoma methods, such as those described by Kohler and Milstein, Nature, 256:495 (1975) or Harlow and Lane. Antibodies, A Laboratory Manual. Cold Spring Harbor Publications, New York, (1988). In a hybridoma method, a mouse or other appropriate host animal, is typically immunized with an immunizing agent to elicit lymphocytes that produce or are capable of producing antibodies that will specifically bind to the immunizing agent. Alternatively, the lymphocytes may be immunized in vitro. Preferably, the immunizing agent comprises SZP. Traditionally, the generation of monoclonal antibodies has depended on the availability of purified protein or peptides for use as the immunogen. More recently DNA based immunizations have shown promise as a way to elicit strong immune responses and generate monoclonal antibodies. In this approach, DNA-based immunization can be used, wherein DNA encoding a portion of SZP, preferably the N- or C-terminal region, is injected into the host animal according to methods known in the art and as described in the examples. An alternate approach to immunizations with either purified protein or DNA is to use antigen expressed in baculovirus. The advantages to this system include ease of generation, high levels of expression, and post-translational modifications that are highly similar to those seen in mammalian systems. Use of this system involves expressing domains of proteins as fusions to the baculovirus surface glycoprotein gp64. The antigen is produced by inserting a gene fragment in-frame between the signal sequence and the mature protein domain of the gp64 nucleotide sequence. This results in the display of the foreign proteins on the surface of the virion. This method allows immunization with whole virus, eliminating the need for purification of target antigens.

Generally, either peripheral blood lymphocytes ("PBLs") are used in methods of producing monoclonal antibodies if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, "Monoclonal Antibodies: Principles and Practice" Academic Press, (1986) pp. 59–103). Immortalized cell lines are usually transformed mammalian cells, including myeloma cells of rodent, bovine, equine, and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies (Kozbor, J. Immunol., 133:3001 (1984); Brodeur et al., "Monoclonal Antibody Production Techniques and Applications" Marcel Dekker, Inc., New York, (1987) pp. 51–63).

The culture medium in which the hybridoma cells are cultured can then be assayed for the presence of monoclonal antibodies directed against SZP. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art, and are described further in the Examples below or in Harlow and Lane "Antibodies, A Laboratory Manual" Cold Spring Harbor Publications, New York, (1988).

After the desired hybridoma cells are identified, the clones may be subcloned by limiting dilution or FACS sorting procedures and grown by standard methods. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, plasmacytoma cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567) or by covalently joining to the immunoglobulin coding sequence all or part of the coding sequence for a non-immunoglobulin polypeptide. Optionally, such a non-immunoglobulin polypeptide is substituted for the constant domains of an antibody of the invention or substituted for the variable domains of one antigen-combining site of an antibody of the invention to create a chimeric bivalent antibody comprising one antigen-combining site having specificity for SZP and another antigen-combining site having specificity for a different antigen.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994, U.S. Pat. No. 4,342,566, and Harlow and Lane, Antibodies, A Laboratory Manual, Cold Spring Harbor Publications, New York, (1988). Papain digestion of antibodies typically produces two identical antigen binding fragments, called Fab fragments, each with a single antigen binding site, and a residual Fc fragment. Pepsin treatment yields a fragment, called the F(ab')$_2$ fragment, that has two antigen combining sites and is still capable of cross-linking antigen.

The Fab fragments produced in the antibody digestion also contain the constant domains of the light chain and the first constant domain of the heavy chain. Fab' fragments differ from Fab fragments by the addition of a few residues at the carboxy terminus of the heavy chain domain including one or more cysteines from the antibody hinge region. The F(ab')$_2$ fragment is a bivalent fragment comprising two Fab' fragments linked by a disulfide bridge at the hinge region. Fab'-SH is the designation herein for Fab' in which the cysteine residue(s) of the constant domains bear a free thiol group. Antibody fragments originally were produced as pairs of Fab' fragments which have hinge cysteines between them. Other chemical couplings of antibody fragments are also known.

An isolated immunogenically specific paratope or fragment of the antibody is also provided. A specific immunogenic epitope of the antibody can be isolated from the whole antibody by chemical or mechanical disruption of the molecule. The purified fragments thus obtained are tested to determine their immunogenicity and specificity by the methods taught herein. Immunoreactive paratopes of the antibody, optionally, are synthesized directly. An immunoreactive fragment is defined as an amino acid sequence of at least about two to five consecutive amino acids derived from the antibody amino acid sequence.

One method of producing proteins comprising the antibodies of the present invention is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the antibody of the present invention, for example, can be synthesized by standard chemical reactions. For example, a peptide or polypeptide can be synthesized and not cleaved from its synthesis resin whereas the other fragment of an antibody can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant G A (1992) Synthetic Peptides: A User Guide. W. H. Freeman and Co., N.Y. (1992); Bodansky M and Trost B., Ed. (1993) Principles of Peptide Synthesis. Springer-Verlag Inc., NY. Alternatively, the peptide or polypeptide is independently synthesized in vivo as described above. Once isolated, these independent peptides or polypeptides may be linked to form an antibody or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776–779 (1994)). The first step is the chemoselective reaction of an unprotected synthetic peptide-α-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site. Application of this native chemical ligation method to the total synthesis of a protein molecule is illustrated by the preparation of human interleukin 8 (IL-8) (Baggiolini M et al. (1992) FEBS Lett. 307:97–101; Clark-Lewis I et al., J.Biol.Chem., 269:16075 (1994); Clark-Lewis I et al., Biochemistry, 30:3128 (1991); Rajarathnam K et al., Biochemistry 33:6623–30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257–267 (1992)).

The invention also provides fragments of antibodies which have bioactivity. The polypeptide fragments of the present invention can be recombinant proteins obtained by cloning nucleic acids encoding the polypeptide in an expression system capable of producing the polypeptide fragments thereof, such as an adenovirus or baculovirus expression system. For example, one can determine the active domain of an antibody from a specific hybridoma that can cause a biological effect associated with the interaction of the antibody with SZP. For example, amino acids found to not contribute to either the activity or the binding specificity or affinity of the antibody can be deleted without a loss in the respective activity.

For example, in various embodiments, amino or carboxy-terminal amino acids are sequentially removed from either the native or the modified non-immunoglobulin molecule or the immunoglobulin molecule and the respective activity assayed in one of many available assays. In another example, a fragment of an antibody comprises a modified antibody wherein at least one amino acid has been substituted for the naturally occurring amino acid at a specific position, and a portion of either amino terminal or carboxy terminal amino acids, or even an internal region of the antibody, has been replaced with a polypeptide fragment or other moiety, such as biotin, which can facilitate in the purification of the modified antibody. For example, a modified antibody can be fused to a maltose binding protein, through either peptide chemistry or cloning the respective nucleic acids encoding the two polypeptide fragments into an expression vector such that the expression of the coding region results in a hybrid polypeptide. The hybrid polypeptide can be affinity purified by passing it over an amylose affinity column, and the modified antibody receptor can then be separated from the maltose binding region by cleaving the hybrid polypeptide with the specific protease factor Xa. (See, for example, New England Biolabs Product Catalog, 1996, pg. 164.). Similar purification procedures are available for isolating hybrid proteins from eukaryotic cells as well.

The fragments, whether attached to other sequences or not, include insertions, deletions, substitutions, or other selected modifications of particular regions or specific amino acids residues, provided the activity of the fragment is not significantly altered or impaired compared to the nonmodified antibody or antibody fragment. These modifications can provide for some additional property, such as to remove or add amino acids capable of disulfide bonding, to increase its bio-longevity, to alter its secretory characteristics, etc. In any case, the fragment must possess a bioactive property, such as binding activity, regulation of binding at the binding domain, etc. Functional or active regions of the antibody may be identified by mutagenesis of a specific region of the protein, followed by expression and testing of the expressed polypeptide. Such methods are readily apparent to a skilled practitioner in the art and can include site-specific mutagenesis of the nucleic acid encoding the antigen. (Zoller M J et al. Nucl. Acids Res. 10:6487–500 (1982).

As used herein, the phrase "specific binding affinity" refers to a binding reaction which is determinative of the presence of the SZP in a heterogeneous population of proteins, proteoglycans, and other biologics. Thus, under designated conditions, the antibodies or fragments thereof of the present invention bind to a particular proteoglycan (e.g., human or porcine SZP or any variant thereof) or protein core, fragment, or variant thereof and do not bind in a significant amount to other proteins or proteoglycans present in the subject. Furthermore, the antibodies of the present invention have a binding affinity for bovine that is the same as or lower than for human SZP, as measured, for example, in a competitive binding assay, IAsys analysis, or BIAcore analysis. Preferably, in an ELISA, the binding of the antibody of the present invention to bovine SZP is 1–10 times the background level (i.e., comparable to non-specific binding or slightly above non-specific binding), when the binding to a comparable amount of human SZP is 10 or more times background. More preferably, the binding of the antibody of the present invention to bovine SZP is no more than 5 times the background level, whereas the binding affinity for human SZP is more than 15 times background. Even more preferably, the binding of the antibody of the present invention to bovine SZP is no more than 2.5 times the background level, whereas the binding affinity for human SZP is more than 18 times background. Thus, the binding affinity of the antibody for human SZP is preferably at least 3 times greater than the binding affinity for bovine SZP.

In one embodiment of the invention, the antibody or fragment thereof, in addition to binding human SZP, binds SZP from at least one non-human species selected from the group consisting of dog, guinea, pig, and rabbit. Thus, in various embodiments the antibody shows cross-reactivity for SZP derived from various species.

Selective binding to an antibody under such conditions may require an antibody that is selected for its specificity for a particular protein, proteoglycan, or variant, fragment, or protein core thereof. A variety of immunoassay formats may be used to select antibodies that selectively bind with a particular protein, proteoglycan, or variant, fragment, or protein core thereof. For example, solid-phase ELISA immunoassays are routinely used to select antibodies selectively immunoreactive with a protein, proteoglycan, or variant, fragment, or protein core thereof. See Harlow and Lane. Antibodies, A Laboratory Manual. Cold Spring Harbor Publications, New York, (1988), for a description of immunoassay formats and conditions that could be used to determine selective binding. The binding affinity of a monoclonal antibody can, for example, be determined by the Scatchard analysis of Munson et al., Anal. Biochem., 107:220 (1980).

The antibody or fragment of the invention binds either a glycosylated or a non-glycosylated superficial zone protein, or it binds both glycosylated and non-glycosylated forms. Also, the antibody or fragment thereof binds non-reduced (i.e., native) superficial zone protein. Under certain conditions, the antibody or fragment thereof may also bind reduced forms.

The invention also provides an antibody reagent kit comprising the antibody or fragment thereof of the invention and reagents for detecting binding of the antibody or fragment thereof to a ligand. Optionally, the kit further comprises containers containing the antibody or fragment thereof of the invention and containers containing the reagents. Preferably the ligand is SZP or a variant, fragment, or protein core thereof. Particularly, the kit detects the presence of SZP specifically reactive with the antibody or an immunoreactive fragment thereof. The kit optionally includes an antibody bound to a substrate, a secondary antibody reactive with the antigen and/or a reagent for detecting a reaction of the secondary antibody with the antigen. In one embodiment, the kit is an ELISA kit, comprising the substrate, primary and secondary antibodies when appropriate, and/or any other necessary reagents such as detectable moieties, enzyme substrates and color reagents as described above. The diagnostic kit, alternatively, is an immunoblot kit generally comprising the components and reagents described herein. Alternatively, the kit is a radioimmunoassay kit, a Western blot assay kit, an immunohistological assay kit, an immunocytochemical assay kit, a dot blot assay kit, a fluorescence polarization assay kit, a scintillation proximity assay kit, a homogeneous time resolved fluorescence assay kit, an IAsys analysis kit, or a BIAcore analysis kit.

As used throughout, methods of detecting SZP or antigen/antibody complexes, including complexes comprising SZP and optionally the antibody of the present invention, comprise an ELISA (competition or sandwich), a radioimmunoassay, a Western blot assay, an immunohistological assay, an immunocytochemical assay, a dot blot assay, a fluorescence polarization assay (Jolley (1981); Jiskoot et al (1991); Seethala et al. (1998); Bicamumpaka et al. (1998)), a scintillation proximity assay (Amersham Life Science (1995) Proximity News. Issue 17; Amersham Life Science (1995) Proximity News. Issue 18; Park et al. (1999)), a homogeneous time-resolved fluorescence assay (Park et al. (1999); Stenroos et al. (1988); Morrison, 1988)), a IAsys analysis (Edwards and Leatherbarrow (1997)), or a BIAcore analysis (Fägerstam et al. (1992)). Preferably, the antigen/antibody complex is detectably tagged either directly or indirectly. Any desired tag can be utilized, such as a fluorescent tag, a radiolabel, a magnetic tag, or an enzymatic reaction product.

The invention also provides a method of detecting superficial zone protein in a sample, comprising contacting the sample with the antibody or fragment of the present invention, under conditions in which an antigen/antibody complex can form; and detecting the presence of the antigen/antibody complex, wherein the presence of the antigen/antibody complex indicates the presence of superficial zone protein in the sample. Preferably the sample is selected from the group consisting of body fluids, such as synovial fluid, tears, saliva, urine, serum, plasma, and bone marrow, and connective tissue and components thereof, such as synovium, tendon, tendon sheath, ligament, meniscus, intervertebral disk, pericardium, chondrocytes, and articular cartilage. The contacting step of the present method is either in vivo or in vitro.

As used throughout, by "subject" is meant an individual. Preferably, the subject is a mammal such as a primate, and, more preferably, a human. The term "subject" includes domesticated animals, such as cats, dogs, etc., livestock (e.g., cattle, horses, pigs, sheep, goats, etc.), and laboratory animals (e.g., mouse, rabbit, rat, guinea pig, etc.).

The present invention also provides a method of diagnosing a degenerative condition, such as a joint, connective tissue, or blood disorder, in a subject, comprising obtaining a test sample from the subject; detecting superficial zone protein in the test sample; and comparing the amount of superficial zone protein in the test sample with an amount present in a control sample; a modulated amount of superficial zone protein in the test sample indicating the degenerative condition. As used throughout, the terms "degenerative condition" or "degenerative disease" includes a variety of blood, connective tissue, and joint diseases, including, for example, tendonitis, pericarditis, osteoporosis, and degenerative joint disease. The term "degenerative joint condition" or "degenerative joint disease" includes a variety of conditions marked by inflammatory or non-inflammatory joint disease, including arthritic conditions (e.g., osteoarthritis, rheumatoid arthritis, gout, psoriatic arthritis, reactive arthritis, viral or post-viral arthritis, spondylarthritis, juvenile arthritis, and systemic lupus erythematosus), CACP, osteoporosis, and trauma. Such degenerative joint diseases are characterized by morphological, compositional, and metabolic changes in articular cartilage. A subject with a degenerative joint disease may show clinical or subclinical signs of the disease, and thus demonstrate either early or late stages of the disease.

"Osteoarthritis," as used herein, would include both primary and secondary degenerative joint disease, and a subject with osteoarthritis may show any of the early manifestations of osteoarthritis, including, for example, increased water content of the cartilage, increased collagen extractability, increased levels of annexin V, crepitus, and radiologic changes (including joint space narrowing, subchondral sclerosis or cysts, and osteophyte formation), or later manifestations, including, for example, joint pain, joint swelling, joint stiffness, reduced quality and quantity of cartilage matrix, deformity, chondrocalcinosis, and reduced range of motion.

"Rheumatoid arthritis" as used herein refers to inflammatory joint disease in both early and late stages. Signs and manifestations of the early stages include, for example, general fatigue, joint stiffness or aching, synovial inflammation, excessive synovial fluid, joint effusion, osteoporosis in the ends of the bones forming the affected joint or joints, edematous synovial cells, and proliferation of synovial lining cells. In later stages, additional signs and manifestations are detected, including joint pain, redness, swelling, and inflammation. Pannus can be seen in the joints. Cartilage and subchondral bone can be eroded at the articular surface. Changes in the composition of the synovial fluid can occur. Laxity in tendons and ligaments, as well as deformity, can occur and can cause limitations in joint range of motion and joint instability. Furthermore, Rheumatoid Factor(s) can be detected in the subject's blood at both early and late stages of the disease.

As used throughout, a "test sample" is selected from the group consisting of body fluids, such as synovial fluid, tears, saliva, urine, serum, plasma, and bone marrow, and connective tissue and components thereof, such as synovium, tendon, tendon sheath, ligament, meniscus, intervertebral disk, pericardium, chondrocytes, and articular cartilage. The test sample can be obtained by methods well known in the art, including for example, by aspiration or biopsy. As used throughout, a "control sample" comprises either a sample obtained from a control subject (e.g., from the same subject before treatment, or from a second subject without degenerative disease or without treatment) or comprises a known standard.

In the method of diagnosing, the amount of superficial zone protein in the test sample is compared with an amount present in a control sample by contacting the test sample with the antibody of the present invention and detecting the antibody/antigen complex. The contacting step is performed either in vivo or in vitro. One skilled in the art would know or could readily determine normal levels of SZP against which to compare the test sample. For example, SZP (MSF) has been reported to be present in concentration of less than 1 ng/ml in serum and urine. The concentration of SZP in biological fluids is measured using, for example, competition ELISA, RIA, or sandwich ELISA. Optionally, levels are quantified by competition immunoassays in a homogenous format, such as Scintillation Proximity Assay (Amersham Life Science (1995) Proximity News. Issue 17; Amersham Life Science (1995) Proximity News. Issue 18; Park et al. (1999)), Homogeneous Time-Resolved Fluorescence Assay (Park et al. (1999); Stenroos et al. (1988); Morrison, 1988)), and Fluorescence Polarization Assay (Jolley (1981); Jiskoot et al (1991); Seethala et al. (1998)). A homogenous assay format does not require separation of antibody-antigen complex from unbound antibody or antigen, thus eliminating washing/error prone steps and decreasing experimental variations. Optionally, the concentration of SZP in biological fluids is measured when compared to a serial dilution of non-radiolabeled SZP or SZP fragment. SZP fragment can be a fragment purified from biological fluid, enzymatic digestion or recombinant truncated SZP protein.

By "modulation" or "modulating" is meant either an increase or a decrease in SZP levels. Whether the levels are increased or decreased in a subject with a degenerative condition depends on the particular sample and the status of the disease state. For example, with the onset of a degenerative joint disease, SZP levels may transiently decrease in the synovial fluid, only to be followed by a compensatory increase. Such changes may occur when chondrocyte synthesis of SZP decreases early in the disease process and is followed by a compensatory increase in synthesis and/or release by either chondrocytes or synovial cells. As another example, in the synovium or synovial fluid, the degenerative joint condition may be indicated by an elevated amount of superficial zone protein in the test sample but indicated by a decreased level of SZP in articular cartilage or on the articular surface. SZP in the test sample is compared to a control sample by contacting the test sample with the antibody or fragment of the present invention or other antibody to SZP, under conditions that allow formation of an antibody/antigen complex, and the antigen/antibody complex is detected by the various detection methods mentioned above.

The invention further provides a method of screening for subjects who would benefit from treatment for a degenerative joint condition, comprising the steps of obtaining a test sample from each subject; detecting superficial zone protein in the test samples; and comparing the amount of superficial zone protein in the test samples with an amount present in a control sample, a modulated amount of superficial zone protein in the test sample indicating a subject that would benefit from treatment for the degenerative joint condition. This method is useful in identifying subjects who are candidates for treatment when the symptoms of the degenerative joint condition are clinical or subclinical. By "clinical" or "subclinical" is meant a degenerative joint condition that may or may not be accompanied by clinical symptoms such as pain, limited range of motion, radiologic changes in the joint, etc. Thus, the present method is used to identify subjects with very early to late manifestations of the degenerative joint condition so that treatment can be started and further manifestation of the condition can be prevented or reduced. Preferably, the test sample and control sample are selected from the group consisting of synovial fluid, tears, saliva, urine, serum, plasma, and bone marrow, synovium, tendon, tendon sheath, ligament, meniscus, intervertebral disk, pericardium, chondrocytes, and articular cartilage. The modulation in the amount of superficial zone protein in the test sample that indicates a subject that would benefit from treatment for the degenerative joint condition depends upon the test sample selected. For example, in one embodiment of the invention, when the test sample is synovial fluid or synovium, the subjects that would benefit from treatment are indicated by an elevated amount of superficial zone protein in the test samples, but, in another embodiment, when the test sample is articular cartilage or chondrocytes, the subjects that would benefit from treatment are indicated by an decrease in the amount of superficial zone protein in the test samples. Preferably, the superficial zone protein is detected by contacting the test sample with the monoclonal antibody or fragment of the invention.

The invention further provides a method of screening for a substance that modulates levels of superficial zone protein, comprising contacting a test sample with the substance to be screened, wherein the test sample contains superficial zone protein-producing cells; contacting, under conditions in which an antigen/antibody complex can form, the superficial zone protein in the test sample with the antibody or a fragment of the invention; detecting the level of the antigen/antibody complex in the test sample; and comparing the level of the antigen/antibody complex in the test sample with the level of antigen/antibody complex in a control sample; a lower or higher level of the antigen/antibody complex in the test sample indicating a substance that modulates levels of superficial zone protein. The superficial zone protein-producing cells are selected from the group consisting of chondrocytes, synovial cells, pericardial cells, bone marrow cells, and connective tissue cells (e.g., cells from tendon, ligament, meniscus, or intervertebral disk) of any species. Preferably, the cells are mammalian cells. Even more preferably, the mammalian cells are human cells.

The contacting step of the present method is either in vitro or in vivo. Preferably, the superficial zone protein contacted in the sample is secreted by the superficial zone protein-producing cells.

The method of screening, optionally, further comprises contacting the test sample with an agent that increases levels of superficial zone protein, wherein the lower or higher level of the antigen/antibody complex indicates, respectively, a substance that attenuates or potentiates the increase in superficial zone protein. The agent that increases levels of SZP is, for example, a synthetic agent, a cytokine, or growth factor, such as TGFβ, IGF-1, BMP-1, BMP-4, BMP-7 (osteogenic protein-1). The step of contacting the test sample with the agent optionally is before, after, or simultaneously with the step of contacting the sample with the substance to be screened. By "attenuation" is meant a reduction in the increase in SZP level that occurs upon contact of the SZP secreting cell with the agent that increases SZP release or synthesis. By "potentiation" is meant a synergistic or additive effect between the substance to be tested and the agent that increases SZP release or synthesis.

Further provided is a method of screening for a substance that reduces a degenerative condition, such as a degenerative joint condition, in a subject, comprising contacting a first test sample from the subject with the antibody or fragment thereof of the invention, under conditions in which an antigen/antibody complex can form; detecting the level of the antigen/antibody complex in the first test sample; treating the subject with the substance to be screened; contacting a second test sample from the subject with the antibody or fragment of the invention, under conditions whereby an antigen/antibody complex can form; detecting the level of the antigen/antibody complex in the second test sample; and comparing the level of the antigen/antibody complex in the first test sample with the level of antigen/antibody complex in the second test sample, a modulated level of the antigen/antibody complex in the second test sample indicating a substance that reduces the degenerative condition. Alternatively, the test sample is compared to a known standard or to a control sample from a second untreated subject with degenerative disease. The contacting step is performed either in vivo or in vitro. The nature of the observed modulation will vary depending on the test sample selected and the disease state. For example, when the test sample is synovium or synovial fluid, the degenerative joint condition will be indicated by an elevated amount of superficial zone protein in the test sample; and when the test sample is chondrocytes, articular cartilage, or the articular surface, the degenerative joint condition is indicated by a reduced amount of superficial zone protein in the test sample.

Further provided is a method of imaging an articular surface or synovium of a joint, comprising contacting the articular surface of the joint with the antibody or fragment of the invention, under conditions in which an antigen/antibody complex can form on the articular surface, wherein the antibody or fragment thereof is detectably tagged; visualizing the detectable tag in antigen/antibody complexes in a plurality of locations on the articular surface; the visualization of detectable tag in antigen/antibody complexes showing the articular surface of the joint. Such an imaging method is used for the purpose of prognosis, diagnosis, and monitoring of a degenerative joint condition. Thus, the invention further provides a method of diagnosing or monitoring a degenerative joint condition in a subject, comprising imaging one or more articular surfaces in the subject using the method of the invention and comparing the articular surface or surfaces of the subject to a control articular surface. Degenerative changes in the articular surface or surfaces of the subject indicates the degenerative joint condition.

The detectable tag used in the imaging method is, for example, a radio-opaque substance, radiolabel, a fluorescent label, or a magnetic label. The detectable tag, optionally, is selected from the group consisting of gamma-emitters, beta-emitters, and alpha-emitters, gamma-emitters, positron-emitters, X-ray-emitters and fluorescence-emitters suitable for localization.

Fluorescent compounds that are suitable for conjugation to a monoclonal antibody include fluorescein sodium, fluorescein isothiocyanate, phycoerythrin, and Texas Red sulfonyl chloride. See, DeBelder & Wik, 1975, Carbohydrate Research 44:254–257. Those skilled in the art will know, or will be able to ascertain with no more than routine experimentation, other fluorescent compounds that are suitable for labeling monoclonal antibodies.

Suitable radioisotopes for labeling antibodies include Iodine-131, Iodine-123, Iodine-125, Iodine-126, Iodine-133, Bromine-77, Indium-111, Indium-113m, Gallium-67, Gallium-68, Ruthenium-95, Ruthenium-97, Ruthenium-103, Ruthenium-105, Mercury-107, Mercury-203, Rhenium-99m, Rhenium-105, Rhenium-101, Tellurium-121m, Tellurium-122m, Tellurium-125m, Thulium-165, Thulium-167, Thulium-168, Technetium-99m and Fluorine-18. The halogens can be used more or less interchangeably as labels since halogen-labeled antibody fragments and/or normal immunoglobulin fragments would have substantially the same kinetics and distribution and similar metabolism.

The visualization step optionally comprise a means of visualization selected from the group consisting of nuclear magnetic resonance, radioimmunoscintigraphy, X-radiography, positron emission tomography, computerized axial tomography, magnetic resonance imaging, and ultrasonography. For visualization, the subject, for example, is scanned with a gamma ray emission counting machine such as the axial tomographic scanner commercially available under the designation CT (80–800 CT/T) from General Electric Company (Milwaukee, Wis.), or with a positron emission transaxial tomography scanner.

The gamma-emitters Indium-111 and Technetium-99m are detected with a gamma camera and have favorable half lives for imaging in vivo. The antibody, for example, is labeled with Indium-1 or Technetium-99m via a conjugated metal chelator, such as DTPA (diethlenetriaminepentaacetic acid). See Krejcarek et al., 1977, Biochem. Biophys. Res. Comm. 77:581; Khaw et al., 1980, Science 209:295; Gansow et al., U.S. Pat. No. 4,472,509; Hnatowich, U.S. Pat. No. 4,479,930, the teachings of which are incorporated herein by reference.

For purposes of imaging the articular surface or synovium, the antibody is administered by a variety of techniques known in the art, including orally, intravenously, or intra-articularly by injection into the joint to be visualized. The antibody optionally is administred in a carrier pharmaceutically acceptable to the subject. Suitable carriers and their formulations are described in Remington's Pharmaceutical Sciences, 16th ed., 1980, Mack Publishing Co., edited by Oslo et al. Typically, an appropriate amount of a pharmaceutically-acceptable salt is used in the formulation to render the formulation isotonic. Examples of the pharmaceutically-acceptable carrier include saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered.

Suitable carriers for oral administration of the antibody or fragment thereof include one or more substances which may also act as flavoring agents, lubricants, suspending agents, or as protectants. Suitable solid carriers include calcium phosphate, calcium carbonate, magnesium stearate, sugars, starch, gelatin, cellulose, carboxypolymethylene, or cyclodextrans. Suitable liquid carriers may be water, pyrogen free saline, pharmaceutically accepted oils, or a mixture of any of these. The liquid optionally also contains other suitable pharmaceutical additions such as buffers, preservatives, flavoring agents, viscosity or osmo-regulators, stabilizers or suspending agents. Examples of suitable liquid carriers include water with or without various additives, including carboxypolymethylene as a pH-regulated gel. The antibody or fragment thereof may be contained in enteric coated capsules that release the agent into the intestine to avoid gastric breakdown. For parenteral administration of the antibody or fragment thereof, a sterile solution or suspension is prepared in saline that may contain additives, such as ethyl oleate or isopropyl myristate, and can be injected for example, into subcutaneous or intramuscular tissues, as well as intravenously or intra-articularly. Alternatively, the antibody or fragment thereof is microencapsulated with either a natural or a synthetic polymer into microparticles, which releases the antibody or fragment thereof.

The amount of antibody or fragment thereof administered or the schedule for administration will vary among individuals based on age, size, weight, condition, the joint to be assessed, mode of administration, the imaging system, and the degree of degenerative joint disease. One skilled in the art will realize that dosages are best optimized by the practicing physician and methods for determining dosage are described, for example in Remington's Pharmaceutical Science, 16th ed., 1980, Mack Publishing Co., edited by Oslo et al. Guidance in selecting appropriate doses for antibodies is found in the literature on therapeutic uses of antibodies, e.g., Handbook of Monoclonal Antibodies, Ferrone et al., eds., Noges Publications, Park Ridge, N.J., (1985) ch. 22 and pp. 303–357; Smith et al., Antibodies in Human Diagnosis and Therapy, Haber et al., eds., Raven Press, New York (1977) pp. 365–389. A typical dose of the antibody used alone might range from about 1 µg/kg to up to 100 mg/kg of body weight or more per day, and preferably 1 µg/kg to up to 1 mg/kg, depending on the factors mentioned above. An intravenous injection of the antibody or fragment thereof, for example, could be 10 ng–1 g of antibody or fragment thereof, and preferably 10 ng–1 mg depending on the factors mentioned above. For injection into a joint, a typical quantity of antibody ranges from 1 pg to 1 mg. Preferably, the intrarticular injection would be at an antibody concentration of 1–100 µg/ml, and preferably 1–20 µg/ml. Volumes of antibody and carrier will vary depending upon the joint, but approximately 0.5–10 ml, and preferably 1–5 ml, is injected into a human knee and approximately 0.1–5 ml, and preferably 1–2 ml into the human ankle. The delay between administration of the antibody or fragment thereof and the visualization will be predetermined as the time sufficient for formation of antigen/antibody complexes and, preferably, for non-bound antibody to clear from the subject's body or joint.

Also provided by the present invention is a method of monitoring a subject's response to a treatment for a degenerative joint condition. The method comprises the steps of (a) contacting a first test sample from the subject to be monitored with the monoclonal antibody or fragment thereof of the invention, under conditions that allow formation of an antigen/antibody complex; (b) detecting the level of the antigen/antibody complex in the first test sample; (c) treating the subject; (d) contacting a second test sample from the subject with the antibody or fragment thereof, under conditions whereby an antigen/antibody complex can form; (e) detecting the level of the antigen/antibody complex in the second test sample; and (f) comparing the level of the antigen/antibody complex in the first test sample with the level of antigen/antibody complex in the second test sample, a modulated level of the antigen/antibody complex in the second test sample indicating the subject's response to the treatment. The test samples are preferably selected from the group consisting of synovial fluid, tears, saliva, urine, serum, plasma, bone marrow, synovium, tendon, tendon sheath, ligament, meniscus, intervertebral disk, pericardium, chondrocytes, and articular cartilage. The modulation in the amount of superficial zone protein indicates either a positive or a negative effect of the treatment, and the nature of the modulation depends upon the test sample and other factors. For example, in one embodiment of the invention, when the test sample is synovial fluid or synovium, a reduction in the amount of superficial zone protein in the second test sample indicates a positive response to the treatment. In another embodiment, when the test sample is articular cartilage or chondrocytes, an increase in the amount of superficial zone protein in the second test sample indicates a positive response to the treatment.

The first test sample optionally may be obtained prior to, simultaneously with, or after the first treatment. The present method optionally further comprises contacting one or more additional test samples (for example, a third, fourth, fifth, sixth, etc. sample) with the antibody or fragment thereof and detecting the level of the antigen/antibody complex in the additional test sample(s). The level or levels in the additional test sample or samples is compared to the control or to the previous test sample or samples. Thus, in the presence of a single treatment, the short and long term effects on the levels can be monitored. Similarly, with an ongoing treatment regimen, the short and long term effects, as well as the cumulative effect of treatment can be monitored.

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

EXAMPLES

Example 1

Isolation and Purification of Human Superficial Zone Protein (SZP) from Cartilage Human tali were obtained through collaboration with The Regional Organ Bank of Illinois (ROBI) with the approval of the institutional review board (IRB) of the Medical College of Rush Presbyterian St. Luke's Medical Center. Individual entire human tali were submerged in approximately 100–130 ml of medium consisting of Dulbecco's Modified Eagle Medium (DMEM) supplemented with 5% fetal bovine serum, 25–50 µg/ml ascorbic acid and 20 µCi of $^3$H-proline for 18–22 hours in a humidified atmosphere of 5% $CO_2$/air at 37° C. with constant stirring. After the incubation period, the medium (containing $^3$H-proline labeled Superficial Zone Protein (SZP) was harvested and six Complete™ mini protease inhibitor cocktail tablets (Boehinger Mannheim, Gmbh, Germany) were added. Dry guanidinium hydrochloride (GuHCl) was added to the medium to bring the concentration of GuHCl to 4 M. The solution was brought to an initial density of 1.46 gm/ml by the addition of Cesium chloride (0.57 grams per gram of medium). The solution was subjected to equilibrium density gradient ultracentrifugation at 33,000 RPM for 40 hours at 10° C. The resulting gradient was fractionated into five equal portions, designated as D5 at the top to D1 at the bottom of the gradient solution. The D5 fraction was dialyzed against water and brought to 8 M urea, 0.005 M EDTA, 0.15 M sodium chloride, 0.05 M sodium acetate, pH 6.0 by the addition of dry chemicals and acetic acid. This solution was subjected to anion exchange chromatography on DEAE Sephacel equilibrated in 8 M urea, 0.15 M sodium chloride, 0.005 M EDTA, 0.05 M sodium acetate at pH 6.0 and the SZP was eluted from the DEAE in a stepwise fashion using increasing concentrations of sodium chloride of 0.3 M and 0.6 M salt. SZP eluted between 0.3 and 0.6 M sodium chloride. The SZP containing fraction was dialyzed against water, lyophilized, dissolved in column buffer and subjected to column chromatography on Sepharose CL-4B in the presence of 4 M GuHCl, 0.1 M sodium sulfate, 0.005 M EDTA and 0.05 M sodium acetate, pH 5.8. The eluate from the column was collected in equal fractions and the fractions were analyzed for the presence of $^3$H-proline by scintillation counting. Putative SZP containing fractions were pooled, dialyzed against water, lyophilized, dissolved in sample buffer and analyzed by SDS-PAGE to confirm the presence of SZP. This entire procedure was repeated without the presence of $^3$H-proline and the final lyophilized material was used as antigen for the production of monoclonal antibodies.

SZP purified from culture media of human tali had similar characteristics to bovine SZP for all of the steps in the purification procedure. SDS-PAGE analysis of purified human SZP revealed a single broad band as visualized by staining with Stains-all, suggesting a highly glycosylated protein. SZP had an apparent molecular mass of 345 kDa compared to globular standards. Putative SZP was subjected to peptide mapping using endoproteinase Lys-C. Two of the resulting 4 peptides were sequenced, and sequences (RGGSIQQYIY (SEQ ID NO:1) and DQYYNIDVPS (SEQ ID NO:2) matched SZP in the nonredundant protein database.

Example 2

Isolation and Purification of Human Superficial Zone Protein (SZP) From Media of Cultures of Chondrocytes and From Synovial Fluid SZP was purified from culture medium or synovial fluid by a combination of affinity chromatography, first on a peanut lectin and then on a monoclonal anti-SZP antibody column. Culture medium or synovial fluid was made 0.5 M in NaCl and 5 mM in EDTA and clarified by centrifugation at 10,000 g for 15 minutes. The supernatant, either 50 ml of culture medium or 5 ml of synovial fluid, was incubated with 5 ml of peanut lectin-agarose beads (Sigma, St. Louis, Mo.) with rotation overnight at 4° C. The lectin beads were washed with 25 ml of 10 mM sodium phosphate, 0.5 M NaCl, 5 mM EDTA, pH 7.5 buffer. The bound SZP was eluted with the same buffer containing 0.4 M lactose. The lectin beads were subsequently washed with the washing buffer containing 1.5 M NaCl and then again with washing buffer containing 0.35 M lactose and 1.5 M NaCl. The majority of the SZP was eluted in the first elution with 0.4 M lactose. This SZP preparation also contained small amounts of fibronectin and albumin.

Like the form of SZP isolated from cartilage slice cultures, the band was stained by Coomassie blue, Stainsall or silver, but usually 10–15 µg of protein was necessary for a detection of the band on the gels. The form of SZP isolated from human synovial fluid had comparable movility on 5% polyacrylamide gels to the form of the molecule isolated from cartilage organ culture. The putative SZP band from the SDS-PAGE gel was excised and subjected to in-gel digestion using trypsin prior to characterization by tandem mass spectrometry. All five resulting peptide spectra matched entries in the nonredundant database for SZP. These were GFGGLTGQIVAALSTAK (SEQ ID NO:3), ETSLTVNK (SEQ ID NO:4), ETSLTVNKETTVETK (SEQ ID NO:5), DQYYNIDVPSR (SEQ ID NO:6), and CFESFER (SEQ ID NO:7). This confirmed the identity of the SZP isolated from human synovial fluid by the peanut lectin affinity column.

The SZP preparations were further purified on an anti-SZP monoclonal antibody affinity column. Five ml of Sepharose CL-2B (Sigma, St. Louis, Mo.) was activated with CNBr as described by March et al. (1974)) and incubated with 2.5 mg each of purified monoclonal antibodies S6.79 and 17.109. Residual reactive sites were blocked with 0.1 M Tris, pH 9.8 for 1 h and the beads washed with 2 M urea, followed by 1 M NaCl in PBS buffer. Antibody conjugation efficiency to the Sepharose beads was greater than 80%. SZP preparations were made 1 M in NaCl and 1% Triton and incubated with the anti-SZP beads overnight with rotation at 4° C. The beads were washed with PBS containing 1 M NaCl and 1% Triton. The bound SZP was eluted with 2 M guanidine hydrochloride, pH 7.5. The eluted SZP was dialyzed against 0.5 M NaCl, 10 mM sodium phosphate, pH 7.5 and stored at −20° C. These preparations yielded a single band of SZP at 345 kDa by SDS-PAGE.

Example 3

Production of Monoclonal Antibodies to Non-Modified SZP

A. SZP Immunization

Purified human SZP, which was prepared as described in Example 1, was used as the antigen for immunization for antibody production. Two 8 week old female SJL mice were immunized using either a RIMMS (Repetitive Immunization Multiple Sites) protocol or a conventional immunization regime (e.g., Su et al, 1999).

For RIMMS, one 8-week-old female SJL mouse (Jackson Laboratories, Bar Harbor, Me.) was immunized on days 0, 3, 5, 7 and 11, following the RIMMS immunization regime (Kilpatrick et al., 1997). The mouse was anesthetized with isofluorane prior to each series of immunizations. Twelve sites proximal to the draining lymph nodes were injected subcutaneously with 50 µl per site of antigen/adjuvant mixture. Six of the sites received antigen diluted 1:1 with complete Freund's adjuvant (FCA; Life Technologies, Inc., Grand Island, N.Y.) and the six juxtaposed sites received antigen diluted 1:1 in RIBI adjuvant (RIBI ImmunoChem. Research, Inc., Hamilton, Mont.).

One eight week old female SJL mouse was immunized, using a conventional immunization regimen (e.g., Su et al, 1999), on day 0, 14, 21, and 24. The immunizations on day 0 and 14 were I.P. with the antigen diluted 1:1 in RIBI adjuvant. The day 21 immunization was I.V. with the antigen diluted in sterile PBS. The final immunization was I.P. with the antigen diluted in sterile PBS.

B. PEG Induced Somatic Fusion Protocols

Mice were sacrificed, and a single cell suspension was prepared from either the spleen or the lymph node cells (brachial, axillary, superficial inguinal and popliteal). These cells were combined at a ratio of 2.5:1 with the modified myeloma cell line P3XBcl-2–13 (Kilpatrick et al., 1997). Somatic fusion was performed using 1 ml of 50% polyethylene glycol 1500 (Boehringer Mannheim, GmbH, Germany). Pelleted cells were resuspended in media containing 40% Excell-610 (JRH Biosciences, Lenexa, Kans.), 40% RPMI 1640, 10% FBS, 10% Origen Cloning Factor (Igen, Rockville Md.), 2 mM L-glutamine, 100 µg/ml penicillin, and 0.01 mM 2-ME, plated out at 1 ml per well in 24 well plates, and incubated overnight at 37° C. After 24 hours, 1 ml of selection media containing a 2×concentration of HAT (0.1 mM hypoxanthine, 0.16 mM thymidine, and 4 mM aminopterin, GibcoBRL) prepared in the above media, was added to each well. After one week in culture, media was changed to contain HT (0.1 mM hypoxanthine, 0.16 mM thymidine, GibcoBRL).

Example 4

Screening of Potential Monoclonal Antibodies to SZP

Attempts to generate hybridomas using SZP derived from human tali conditioned media as immunizing antigen resulted in 7 ELISA-reactive wells out of 144 growth-positive wells. Upon preliminary ELISA screening, 5 of 7 hybridomas showed low but specific immunoreactivity against SZP with no reactivity against aggrecans isolated from either bovine nasal cartilage or rat chondrosarcoma. Following the primary ELISA, the ELISA-reactive hybridomas were further screened by chondrocyte immunocytochemistry using chondrocyte subpopulations, a protocol adapted from a fluorescence microtiter screening assay to isolate immunocytochemistry-reactive antibodies (Su, 1997). Uncloned hybridoma 4.23 was selected based on its immunostaining on the superficial chondrocytes and negative for the deep zone chondrocytes. Hybridoma GW4.23, secreting IgG1, was isolated from limiting dilution cloning of parent hybridoma 4–23.

A. Primary ELISA Screening

Aggrecan isolated from bovine nasal cartilage (BNS) and rat chondrosarcoma (RCS), which served as negative controls, were resuspended in 0.1M Tris pH 8.0, aliquoted 1 ml/vial, and frozen at −80° C. The plates were then coated with 3 $\mu$g/ml of either SZP, BNS, or RCS. Antigen was diluted in carbonate coating buffer, pH 9.2–9.6, and plated 100 $\mu$l/well on EIA/RIA plates from Costar. The plates were incubated for 2 hr at 37° C. Then blocked with 100 $\mu$l/well of TBS containing 5% normal goat serum and 1 mg/ml PEG for 30 min at 37° C. 100 $\mu$l/well of tissue culture media corresponding to each individual well of the fusion plates were added and incubated for 1 hr at 37° C. The plates then were washed 3×with 200 $\mu$l/well of 1×TBS+1% Tween 20. 100 $\mu$l/well of secondary antibody G$\alpha$M-IgG alkaline phosphatase conjugated diluted 1:1000 in blocking buffer were added. Plate was then incubated for 1 hr at 37° C. The plates were then developed with Sigma 104 phosphatase substrate and the color change was read at 15 and 30 min.

All wells were tested for binding, and all were growth positive. Seven wells were selected as positive from the conventional immunization and fusion. These seven wells were plated at 30 cells per plate in a 96-well plate for limiting dilution cloning. Four wells from the RIMMS fusion that were selected as positive were also plated to clone by limiting dilution. Aliquots of the supernatants were further analyzed in the subsequent assays.

B. Antibody Staining of Chondrocyte Cultures

Thin slices of articular cartilage from human tali were manually dissected from the superficial, middle and deep zones of the cartilage and placed in DMEM. The slices from the middle zone were discarded. The cartilage slices from the superficial and deep zones were treated separately with 0.2% pronase in DMEM supplemented with 5% fetal bovine serum for 1.5 hours at 37° C. (Aydelotte and Kuettner, Connect Tissue Res. 18:205–222, 1988; Aydelotte et al. Connect Tissue Res 18:223–234, 1988; Schumacher et al., J. Orthop. Res.17:110–120, 1999). The slices were then rinsed extensively with DMEM and treated further with 0.025% Collagenase P for 18–22 hours in DMEM supplemented with 5% fetal bovine serum. The resulting chondrocyte suspensions were centrifuged at 1000 RPM for 15 minutes in order to pellet the cells. The chondrocytes were washed in DMEM three times and centrifuged as stated above to collect the cells. The number of chondrocytes in each sample was determined by counting the cells on a hemacytometer.

Chondrocytes from the superficial and deep zones were seeded separately into a 96 well tissue culture plate at high density (250,000 cells/cm$^2$) in medium consisting of DMEM supplemented with 10% fetal bovine serum. The cells were allowed to attach overnight and refed with medium consisting of DMEM supplemented with 10% fetal bovine serum and 50 $\mu$g/ml ascorbic acid. After three days in culture the cells were refed with medium plus $10^{-6}$ M monensin for four hours in order to prevent secretion through the Golgi apparatus. At the end of the incubation period the cells were rinsed briefly in phosphate buffered saline (PBS) and fixed with a solution of 4% paraformaldehyde in PBS, pH 7.4 for five minutes at room temperature. The cells were rinsed in PBS and permeabilized with a solution of 0.1% Triton-X 100® (Sigma Chemical Co., St. Louis, Mo.) for five minutes at room temperature. The cells were rinsed in PBS and non-specific binding sites were blocked with a solution of 1% bovine serum albumin (BSA) and 1% normal goat serum for 20 minutes at room temperature. The cells were rinsed in PBS and pairs of wells containing cells from the superficial and deep zones were incubated with different hybridoma media, potentially containing a monoclonal antibody to SZP for 45 minutes at room temperature. The cells were rinsed in PBS and incubated with a goat anti-mouse rhodamine conjugated IgG diluted 1:50 with PBS for 45 minutes at room temperature. The cells were rinsed in PBS and examined by fluorescence microscopy. Any pair of wells containing cells from the superficial and deep zone that was positive in the chondrocytes from the superficial zone and negative in the chondrocytes from the deep zone was considered as a positive reaction as a monoclonal antibody to SZP. Four monoclonal antibodies that were positive for the superficial chondrocytes and negative for the deep chondrocytes were obtained. They were designated as GW 3.15, GW 4. 10, GW 4.23 and GW 5.15.

C. Direct ELISA for Human SZP

A 96 well ELISA plate was coated overnight at 4° C. with conditioned media from human talar superficial chondrocytes or deep chondrocytes in the presence of 20 mM NaHCO$_3$/Na$_2$CO3, pH 9.2. All wells were rinsed and incubated with the various hybridoma media for 1 hour at room temperature. The wells were rinsed and incubated with a horseradish peroxidase conjugated goat anti-mouse IgG for 1 hour at room temperature. The wells were rinsed and color development was achieved using hydrogen peroxide and o-phenylenediamine as the chromogenic substrate. Plates were read with an automatic ELISA plate reader. Any pair of wells containing conditioned media from chondrocytes from the superficial zone and chondrocytes from the deep zone in which there was a positive result for the superficial chondrocytes and not the deep chondrocytes was considered positive for SZP.

This method was also used to test samples of human synovial fluids from normal donors and patients with osteoarthritis (OA) and rheumatoid arthritis (RA). Direct ELISA of samples of synovial fluids from normal donors, patients with osteoarthritis and patients with rheumatoid arthritis revealed that SZP is elevated in synovial fluids from patients with OA or RA compared to normal synovial fluid.

D. Immunohistochemistry of Human Knee and Ankle Cartilage

Samples from full thickness slices of cartilage and thin slices from the superficial zone from the articular surface from human femoral condyle and talar dome cartilage were obtained within 24 hours of the death of the donor. Cartilage samples were fixed in 4% paraformaldehyde/PBS for 30 minutes at room temperature and rinsed in PBS. Vertical frozen sections and paraffin embedded sections were obtained from samples of the full thickness of cartilage from human knee and ankle cartilages. Horizontal frozen sections and paraffin embedded sections were obtained from the thin slices of cartilage from the superficial zone. Some cartilage samples were pre-treated with monensin at a concentration of $10^{-6}$ M for four hours before fixation. Sections of cartilage were rinsed in PBS, permeabilized in 0.1% Triton-X 100® (Sigma Chem. Co., St. Louis, Mo.) for five minutes at room temperature and rinsed in PBS. Non-specific binding sites were blocked in a solution of 1% BSA, 1% normal goat serum for 20 minutes at room temperature. The sections were rinsed in PBS and incubated with the monoclonal antibody GW 4.23 (MAb GW 4.23) for 45 minutes at room temperature. The sections were rinsed in PBS and incubated with a horseradish peroxidase conjugated goat anti mouse IgG for 45 minutes at room temperature. The sections were rinsed in 0.05 M Tris, pH 7.6 and positive SZP sites were visualized using hydrogen peroxide and diaminobenzidine as the chromogenic substrate. Alternatively, sections for immunohistochemistry were tested using the Pierce Immunopure® ABC Alkaline Phosphate mouse IgG staining kit (Pierce, Rockford, Ill.), following all manufacturer's directions.

Using MAb GW 4.23, the chondrocytes in the superficial zone of articular cartilage from knee and ankle samples were positive for SZP whereas the chondrocytes in the middle and deep zones were non-reactive. A thin layer of immuno-positive material for SZP was also observed at the articular surface in vertical sections of articular cartilage from both knee and ankle samples. Horizontal sections of the superficial zone also revealed a fine meshwork of immuno-positive material for SZP at the articular surface.

Using all three of the screening protocols, MAb GW 4.23 was the strongest and most specific of all the hybridoma media tested in this experiment.

Example 5

SDS-PAGE and Western Blotting Using MAb GW 4.23

SDS-PAGE was performed on 4–10% gradient separating gels, with a 3.6% stacking gel. Samples for SDS-PAGE were dissolved in sample buffer consisting of 1% SDS, 0.08 M Tris, pH 6.8 containing 16% ethylene glycol and 0.0006% bromophenol blue. All samples were run non-reduced and not boiled. Separated proteins were transferred to nitrocellulose by Western blotting. Western blotting was performed overnight at 250 mAmps in a buffer consisting of 12 mM Tris, pH 7.4, 0.03 mM EDTA and 6 mM sodium acetate. Non-specific binding sites on the nitrocellulose membrane containing the separated proteins were blocked in a solution of 5% non-fat milk in PBS for 30 minutes at room temperature and rinsed in PBS. The nitrocellulose membrane was incubated with MAb GW 4.23 (1:10 dilution) for 1 hour at room temperature. The membrane was rinsed in PBS and incubated with a horseradish-peroxidase conjugated goat anti mouse IgG (1:500 dilution) for 1 hour at room temperature. The membrane was rinsed in 0.5 M Tris pH 7.6 and protein bands specific for the epitope recognized by MAb GW 4.23 were visualized using hydrogen peroxide and 4-chloro-1-napthol as the chromogenic substrate.

Western blotting of purified SZP or samples of human synovial fluids showed a prominent band at 345 kD. Western blots of conditioned medium from slices of the superficial zone from knee and ankle cartilage also showed a protein band of similar mobility as compared to the band for purified SZP.

Example 6

Staining of the Articular Surface of Human Tali Using MAb GW 4.23

Several cylindrical punches of the full thickness of articular cartilage, 8 mm in diameter, were obtained from the talar dome of human ankles. These cartilage plugs were fixed in 4% paraformaldehyde/PBS for 30 minutes at room temperature. The plugs were rinsed in TBS. Non-specific binding sites were blocked with 1% BSA, 1% NGS for 20 minutes at room temperature in TBS. The first antibody, GW 4.23, was applied to different plugs for different amounts of time. Time points of 0, 5, 15, 30, 60, and 120 minutes were used. The plugs were rinsed in TBS and a biotinylated second antibody and avidin-biotin alkaline phosphatase complex applied as stated above for immunohistochemistry. The plugs were incubated with NBT/BCIP substrate used at half strength until maximal color development was achieved. Thirty minutes was chosen as the optimal time of incubation of the first antibody with the cartilage samples and was used for subsequent experiments.

In a different experiment, a matched pair of intact human ankle joints was obtained and one ankle was injected with GW 4.23 (1:10 dilution in DMEM) into the synovial cavity and the other ankle was injected with DMEM. Both joints were incubated for 30 minutes at 37° C. in a humidified chamber. At the end of the incubation times both joints were opened and cylindrical punches of the full thickness of articular cartilage were taken. The punches were fixed in 4% paraformaldehyde/PBS for 30 minutes at room temperature. The punches were rinsed extensively in PBS and then processed as stated above for immunohistochemistry. The punches were placed in NBT/BCIP used at half strength until maximal color development occurred.

In another experiment, a matched pair of normal intact human ankle tali (Collin's grade 0) was obtained and one talus was fixed as stated above and incubated with GW 4.23 (1:10 dilution) for 30 minutes at room temperature. The other talus was fixed and incubated with mouse IgG used at the same concentration of GW 4.23. Both tali were processed as stated above for immunohistochemistry. The tali were placed in NBT/BCIP used at half strength until maximal color development was achieved.

One talus with degenerative changes was obtained (Collin's grade 2). This talus had fissures and a small lesion off to one side of the talar dome. The talus was fixed and processed as stated above using GW 4.23 (1:10 dilution). The talus was placed in NBT/BCIP used at half strength until maximal color development was achieved.

A large piece of cartilage from femoral condyle removed during knee replacement surgery was obtained. The sample was fixed as stated above and processed as stated above using GW 4.23 (1:10 dilution). The sample was placed in NBT/BCIP used at half strength until maximal color development was achieved.

In the experiments outlined here, MAb GW 4.23 was used successfully to stain the articular surface of cylindrical plugs of articular cartilage from human tali. Staining of the articular surface was present at all time points of incubation of MAb GW 4.23 with the tissue samples from as little as 5 minutes incubation with the antibody to as long as 2 hours incubation with the antibody with the optimal time of incubation being 30 minutes. There was no staining of the cartilage when the MAb GW 4.23 was omitted (time point 0). In these experiments, only the surface of the cartilage plug was stained. No staining was seen in the cells or at the deep cut end of the cartilage plug.

Positive staining of the articular surface of cylindrical cartilage plugs was observed when MAb GW 4.23 was injected into an intact human ankle joint prior to fixation or processing of the tissue. No staining was seen in the cells or at the cut edges of the cartilage plug.

Positive staining of the surface of normal human intact ankle tali was observed when MAb GW 4.23 was used in these experiments. The staining at the articular surface was smooth and even and showed no defects at the articular surface. There was also positive staining observed in the synovial tissue surrounding the cartilage. There was no staining at the articular surface of the tali that was treated with the same concentration of a non-specific IgG control.

The articular surface of a human talus showing degenerative changes showed uneven heterogeneous staining when MAb GW 4.23 was used to stain the tissue. Fissures in the articular surface were stained darker than surrounding tissue and areas were present at the surface which were unstained. The lesion site showed very dark staining.

When MAb GW 4.23 was used to stain a piece of cartilage removed from a patient undergoing joint replacement, the surface stained intensely even though there was no superficial zone present. Upon closer examination of the tissue it was found that the staining was due to material deposited at the surface of the damaged cartilage. There was no cellular staining or staining of the matrix within the tissue. All the staining material was at the damaged surface.

Collectively, these experiments demonstrate that a monoclonal antibody to the superficial zone protein can successfully be used to visualize the surface of articular cartilage in both normal and damaged joints as well as the surrounding synovial tissue.

Example 7

Production of Monoclonal Antibodies to Modified SZP

Eight week old, female SJL mice (Jackson Laboratories, Bar Harbor, Me.) were immunized on days 0, 14 and 24 intraperitoneally (IP) with purified human SZP (10 $\mu$g), conjugated with KLH or mixed with hyaluronic acid at 1:10 ratio by weight, in RIBI adjuvant (RIBI, Hamilton, Mont.). Prior to the last IP injection, on day 21, an intravenous injection of the immunizing antigens diluted in PBS was administered to each mouse. On day 25, the mice were sacrificed, splenocytes prepared and somatic fusions were performed as previously described (Su, 1999). Briefly, splenocytes and mouse myeloma cells P3X63BCL2–13 (Kilpatrick et al., 1997) at 2.5:1 ratio were fused using polyethylene glycol 1500 (Boehringer Mannheim GmBH, Germany). Fused cells were resuspended in media containing equal volume of RPMI 1640 (GibcoBRL, Grand Island, N.Y.) and EXCELL-610 (JRH Biosciences, Lenexa, Kans.) supplemented with 1×Origen Hybridoma Cloning Factor (Igen, Gaithersburg, Md.), 10% fetal bovine serum (Hyclone, Logan, Utah), 2 mM L-glutamine, and penicillin/streptomycin. Cells were then plated in 24-well microtiter plates (Costar, Cambridge, Mass.) (1 ml/well), and cultured at 37° C., 5% CO2. Twenty four hours later, 1 ml of 2×HAT selection media [100 $\mu$M hypoxanthine, 0.4 $\mu$M aminopterin, 16 $\mu$M thymidine (GIBCO, Grand Island, N.Y.) in the above media] was added to each well. After 10 days of culture in 1×HAT selection media, media was changed to contain HT (0.1 mM hypoxanthine, 0.16 mM thymidine). Limiting dilution cloning was used for the cloning of hybridomas. Immunoglobulin classes and subclasses were determined using an ELISA subtyping kits (Southern Biotechnology, Birmingham, Ala.) following the manufacturer's instructions.

Example 8

Screening or Potential Monoclonal Antibodies to Modified SZP

When SZP was used as an immunizing antigen without modification, it may not easily elicit T-cell dependent B-cell response. Thus, two approaches were used to modify synovial fluid-derived SZP: (1) conjugation of SZP to a carrier protein, keyhole limpet hemocyanin (KLH) to increase immunogenicity, and (2) mixing SZP with hyaluronic acid (HA), a component present at high concentration (1–3 mg/ml) in synovial fluid, to form complexes, mimicking the form of the molecule most likely to occur in vivo. Both approaches resulted in greater than 95% of 294 growth-positive wells that were positive in ELISA.

A. ELISA Analysis 96-well immunoplates were coated overnight at 4° C. with purified SZP, KLH, peanut lectin in 0.1M sodium bicarbonate buffer containing 0.5M NaCl at pH 9.6. After the plates were washed in PBS, all remaining procedures were carried out at room temperature. Following 30 minutes incubation of immunoplates with blocking buffer (1% BSA in PBS), purified antibodies (1 $\mu$g/ml) were added to the wells and incubated for 1 h. Plates were then washed 3 times with PBS plus 0.1% Triton X-100 (PBST), and goat anti-mouse IgG conjugated with either alkaline phosphatase or horseradish peroxidase (Southern Biotechnology, Birmingham, Ala.) diluted 1/1000 in blocking buffer was added for 1 h incubation. The plates were washed as above and appropriate substrate (Sigma alkaline phosphate substrate or K-blue substrate) was added. Following color development immunoreactivity was measured at 405 nm or 650 nm in a microplate reader (UV max™, Molecular Devices, Menlo Park, Calif.).

Ten ELISA-reactive hybridomas were selected from each immunization and further analyzed by Western blotting and immunohistochemistry. Subsequently, hybridomas that showed different immunoreactivity profiles were cloned by limiting dilution cloning. The ELISA data from GW4.23, a monoclonal antibody derived from non-modified SZP immunization, and a control antibody are represented in FIG. 1. MAb S6.79, derived from SZP-KLH immunization, S13.233 and S17.109, derived from immunization with a mixture of SZP and hyaluronic acid (SZP-HA), show strong immunoreactivity against SZP purified from both synovial fluid (SZP-sf) and articular cartilage (SZP-ac), with no cross-reactivity against KLH or lectin. GW4.23 also shows specific but lower immunoreactivity against SZP from both preparations. S13.52, raised against synovial fluid derived-SZP-HA complex, is the only monoclonal antibody that shows differential reactivity against SZP from different sources. There was no immunoreactivity with the negative control antibody 129R10, a monoclonal antibody against glutathione S-transferase.

B. Chondrocyte Immunocytochemistry

The superficial, middle and deep zones were manually dissected from the articular cartilage of human tali. The slices from the middle zone were discarded. The cartilage slices from the superficial and deep zones were treated separately with 0.2% pronase in DMEM supplemented with 5% FBS for 1.5 hours at 37° C. The slices were then treated with 0.025% Collagenase P for 18 hours in DMEM supplemented with 5% FBS. The superficial and deep zone cells were washed and seeded into the wells of a 96 well tissue culture plate at high density (250,000 cells/cm$^2$). The cells were allowed to attach overnight and fed with medium (DMEM, 10% FBS and 25 µg/ml ascorbic acid). Monensin ($10^{-6}$ M) was added to the cultures for the last four hours of culture. At the end of the incubation period the cells were rinsed briefly in PBS, fixed with 4% paraformaldehyde and permeabilized with 0.1% Triton-X 100® for five minutes at room temperature. The cells were incubated with 1% bovine serum albumin and 1% normal goat serum for 30 minutes at room temperature in order to block non-specific binding sites. Pairs of wells containing cells from the superficial and deep zones were incubated with media from the seven ELISA-positive hybridoma wells, rinsed and incubated with a goat anti mouse rhodamine conjugated IgG diluted 1:50 with PBS. The cells were examined by fluorescence microscopy.

C. Immunolocalization of SZP in Human Articular Cartilage

Full thickness cartilage slices were collected from the talar dome of organ donors within 24 hours of death. Frozen sections of the cartilage slices were cut perpendicular to the articular surface. The sections were fixed with 10% formalin/PBS for 5 minutes and washed in 50 mM Tris, 0.1 M NaCl, pH 7.5. Sections were treated with 0.5% testicular hyaluronidase (Sigma), 1% BSA in PBS for 30 minutes to facilitate antibody penetration in the cartilage tissue and then washed with PBS. They were treated with purified SZP monoclonal antibodies for 2 hours at room temperature and washed with PBS-0.05% Tween. The sections were incubated with a goat-anti-mouse IgG horseradish peroxidase conjugate (Pierce Chemical Co., Rockford Ill.) for 1 hour and washed as above with PBS-Tween buffer. Peroxidase activity was detected with hydrogen peroxide and diaminobenzidine substrates.

Example 9

SDS-PAGE and Western Blotting Using Antibodies to Modified SZP

Purified human SZP (0.25 µg/lane), synovial fluids (0.25 µl human and 1 µl bovine, dog, guinea pig, or rabbit samples), human plasma (1 µl) or human serum (1 µl) were separated by electrophoresis on 3–8% Nu-PAGE Tris acetate gel (Invitrogen, Carlsbad, Calif.) and transferred onto nitrocellulose using Nu-PAGE non-reduced gel buffer system following the manufacturer's instructions. Blots were incubated in blocking solution [5% non-fat dry milk in Tris-buffered saline-Tween (TBST: 50 mM Tris-HCL pH 7.5, 150 mM NaCl, 0.05% Tween-20)]. After brief washes with TBST, the filters were then reacted with SZP monoclonal antibody (1:5 to 1:20 dilution of culture media or 0.25 to 1 µg/ml purified antibody) for 1 hr at room temperature followed by extensive washes with TBST. Blots were then incubated with Goat anti-mouse antibody conjugated with horseradish peroxidase (Southern Biotech, Birmingham, Ala.) for 1 hr, washed with TBST, and developed using the ECL procedure (Amersham, Arlington Heights, Ill.). Unlike the MAb GW4.23, the antibodies generated to modified SZP were able to detect SZP after reduction and boiling; however, they often had stronger signals on Westerns if the preparations were not reduced. Western blotting using MAb S6.79 (0.4 µg/ml) and S17.109 shows strong immunoreactivity against SZP purified from both cartilage and synovial fluid. S13.233 (at 1 µg/ml) also gave a similar staining pattern but the intensity was weaker.

Some of the antibodies were able to detect SZP in plasma and serum. The antibodies detected at least two different forms of the SZP molecule, the large form of the molecule at 345 kDa. S6.79, S17.109, S13.52, S13.233, and GW4.23 all detected a 345 kDa form of SZP in synovial fluid. S6.79, S13.52 and S13.233 are able to detect this form of the molecule in plasma and serum. The amount of SZP appeared to be substantially greater in synovial fluid than in plasma or serum.

Example 10

Preparation of Proteolytic SZP Fragments and Assignment of Epitope-containing Domain A modification of the method of Su et al. (Hybridoma 1995;14(4)383–390) is used to assign the epitope-containing domain of SZP. Purified SZP is reduced and alkylated by incubating the protein in 6M guanidine-HCl, 0.5 M Tris-HCl, 10 mM EDTA and 20 mM dithiothreitol (pH 8.6) for 1 h at 37° C. under nitrogen, followed by addition of 4-vinylpyridine to 50 mM for 30 min at room temperature. The pyridylethylated material is desalted by HPLC with a BU300 column (2.1×30 mm, Brownlee, Foster City, Calif.) using a linear gradient of acetonitrile (16–64%) in 0.1% trifluoroacetic acid (TFA) over 30 min. The eluted protein is then digested with sequencing grade Lys-C (Wako, Richmond, Va.) in 0.1M Tris-HCl (pH 8.5) for 16 h at room temperature, with an enzyme:substrate ratio of 1:100. The Lys-C generated peptides are then separated and isolated on the BU300 column using a linear gradient of acetonitrile (8–64%) in 0.1% TFA over a 40 min period. Peptide fragments are dried by flushing with nitrogen and are then resuspended in TBS. Automated Edman degradations are performed using the Applied Biosystems 477A liquid-pulse sequencer (Applied Biosystem, Foster City, Calif.) equipped with a 120A PTH analyzer for the identification of phenylthiohydantoin amino acids.

The SZP protelytic fragments separated by HPLC are used for coating an ELISA plate for reaction with anti-SZP antibody. The fragment that is recognized by anti-SZP is identified as the epitope-containing domain.

Example 11

Antibody Affinity Measurements

A. BIAcore analysis

BIAcore technology and its use in characterizing intermolecular interactions has previously been described (Fagerstam et al. (1992)). The BIAcore 2000 system, CM5 sensor chips, P-20 surfactant, the coupling kit which contained N-hydroxysuccinimide, N-ethyl-N'-(3-diethylaminopropyl)-carbodiimide, ethanolamine hydrochloride pH 8.5, and rabbit anti-mouse FC-γ is from Pharmacia Biosensor AB (Uppsala, Sweden). All other chemicals are reagent grade. The BIAcore running buffer used for immobilization and binding studies contains 10 mM HEPES (pH 7.4), 150 mM NaCl, 0.05% volume of a 10% P-20 surfactant solution.

Carboxyl groups of the BIAcore CM5 sensor chip hydrogel matrix is activated for 7 min with a mixture of 50 mM N-hydroxysuccinimide and 200 mM N-ethyl-N'-(3-diethylaminopropyl)-carbodiimide. Rabbit anti-mouse Fc-γ (RAMfc) antibody is diluted to 40 µg/ml in 10 mM sodium acetate pH 5.0 then is injected onto the sensor chip for 3 min at a flow rate of 5 µl/min. Unreacted groups are then deactivated with a 7-min injection of 1 M ethanolamine hydrochloride pH 8.5. To determine binding constants, antibodies are injected over the RAMfc at 5 µl/min. for 4 min. The flow is then increased to 40 µl/min and dilutions of human SZP and bovine SZP are injected for 1 min. The surface is regenerated with 100 mM HCl. Binding constants are determined using BIAevaluation software.

B. IAsys Analysis

The binding characteristics of the anti-SZP monoclonal antibodies were measured using resonant mirror technology on an IAsys instrument (Affinity Sensors, Cambridge, England, UK). Biotin-conjugated cuvettes (Affinity Sensors) were used and all experiments were performed at 23° C. Sixty µg of SZP was biotinylated with 300 µg sulfo-N-hydroxysuccinimidyl ester (Pierce Chemical Co., Rockford, Ill.) in 1 ml of 0.1 M sodium carbonate buffer pH 9 for 1 hr. The reaction was terminated by the addition of 0.1 M Tris buffer pH 7.5 and dialyzed against PBS-Tween 0.05% (PBST). Neutraavidin (Pierce Chemical Co., Rockford, Ill.) at 50 µg/ml in PBST was incubated with the biotin-cuvettes for 10 minutes and washed with PBST. Biotinylated SZP (25 µg/ml) was captured on the neutraavidin-coated biotin cuvettes for 10 minutes and washed with PBST. Different monoclonal antibodies were tested in the cuvettes for their ability to bind to the SZP-coated cuvettes at the following concentrations, 50, 20, 10, 5, 2, and 1 µg/ml. Association experiments were performed for 10 minutes followed by a dissociation phase for 10 minutes after a PBST wash. The cuvettes were stripped of residual antibodies between each antibody binding experiment with 10 mM HCl for 2 minutes and then washed with PBST. Binding and dissociation kinetics were calculated using Affinity Sensors FASTfit software. The association rate constant was calculated as the slope of a linear plot of association rates (Y) versus antibody concentrations (X). The dissociation rate constant was the Y intercept from the same line. The dissociation constant ($K_D$) for the antibody was calculated from the dissociation rate constant divided by the association rate constant ($k_{dissoc}/k_{assoc}$).

Example 12

Quantitation of SZP Using Homogenous Formats

A. Scintillation Proximity Assay (SPA)

SZP antibody, radiolabeled (beta emitter) SZP or SZP fragment and the scintillant-embedded polyvinyl toluene beads conjugated with anti-mouse or protein A are mixed together. When radiolabeled SZP or SZP fragment captured by anti-SZP, the beta emitter are brought to the proximity of scintlillant-embedded beads, resulting in the emission of light that is measured by a scintillation counter.

B. Homogeneous Time-resolved Fluorescence Assay (HTRFA)

Biotinlyted SZP or SZP fragment, lanthanide chelate-labeled anti-SZP (fluorescence energy donor) and streptavidin conjugated with the energy acceptor are incubated together to allow the energy donors to be in the proximity of energy acceptors. Donor/acceptor pairs may include for example, Eu/allophycocyanin (or Cy5) or Terbium (Tb)/tetramethylrhodamine. Upon excitation of the donor, the specific energy is transferred from the donor to the acceptor, and the resultant fluorescent signals is measured by a time-resolved fluorometer.

C. Fluorescence Polarization Assay (FPA)

Fluorescent labeled SZP fragment (<30 kDa) and SZP antibody are mixed together to allow the antibody binding to SZP fragment. After the binding reaches equilibrium, the immune complex, due to increased in mass, tumbles more slowly, thus, yielding a polarized fluorescence signal that is measured by a fluorescent polarization meter.

Example 13

DNA-based Immunization for the Production of SZP Monoclonal Antibodies

DNA plasmid preparation, DNA/gold particle bullets and delivery of DNA bullets to mouse epidermis have previously been reported (Kilpatrick et al., 1998; Eisenbraun et al., 1993; Pertmer et al., 1996). DNA encoding the N- or the C-terminal region of SZP is cloned into the Alpha+vector that has human Fc cDNA inclusion (Kaplan et al., 1997). The Alpha+SZP/Fc plasmid is transfected into E. coli and DNA is prepared from a selected clone. After DNA/gold particle bullets are prepared, DNA/gold particles are propelled into the shaved thorastic and abdominal regions of mice using a helium-driven Accell gene gun (PowerJet Vaccines, Incorp. 585 Science drive, Suite C, Madison, Wis. 53711). Following the primary immunization, mice receive one to four booster immunization/s within 8–11 days. On the day of fusion (day 9–13), lymphocytes harvested from axillary, brachial and superficial inquinal nodes are prepared and fused with myeloma cells following a previously published protocol (Su et al, 1999).

Example 14

Immunization via Recombinant Baculovirus Displaying SZP-Fusion Proteins for the Production of SZP Monoclonal Antibodies A. Generation of SZP Fusion Transfer Plasmids The Baculovirus fusion protein is produced using the BacVector Virus Display system from Novagen (Madison, Wis.). Cloning, subcloning and sequencing of DNA are carried out using standard protocols (Sambrook et al., 1989). The amino-terminal domains of human SZP are amplified and cloned into the Kpn I site of the pBACsurf I vector. Positive plaques are selected based on anti-gp64 staining of both native gp64 and gp64 fusion bands in Western blot analysis (Lindley et al. J. Immunological Methods 2000;234:123–135. The virus is then scaled up to a 150 ml suspension culture ($1 \times 10^6$ cells/ml), and incubated on a shaker for 3 days at 27° C. For generation of antigen for immunizations, 450 ml of Sf9 cells at $1 \times 10^6$ cells/ml are infected with relevant virus, at a multiplicity of infection (MOI) of 0.1, and grown for 3 days at 27° C. To harvest virus, the culture supernatant is cleared by high-speed centrifugation for 3 hr at 61,000×g. The virus pellet is resuspended in phosphate buffered saline (PBS) and filtered through a 0.2 µM filter. Virus is diluted in PBS and the mice are immunized as described in Example 2 using the RIMMS immunization regime detailed below. The total amount of antigen used for immunizations is approximately 15 µg of the SZP.

B. ELISA Screening

Primary ELISA screenings are performed using previously published procedures (Harlow & Lane 1988). High binding EIA plates (Corning/Costar Corning, N.Y.) are coated with whole cell lysates from Sf9 cells infected with either a control virus, or the SZP-fusion virus to allow subtractive comparisons. Lysates are prepared from cells infected at a multiplicity of infection (MOI) of 1 pfu/cell at 48 hr post infection. Infected cells are pelleted and subjected to repeated freeze-thaw cycles in a dry ice ethanol bath. The lysates are then diluted 1:10 in carbonate coating buffer and 100 µl per well are incubated at 37° C. for 1 hr. Plates are blocked with 100 µl well of Tris buffered saline (TBS), containing 5% normal goat serum and 1% PEG for 1 hr at 37° C. Undiluted tissue culture supernatant is added at 100 µl/well and incubated at 37° C. for 1 hr. Plates are washed with 1×TBS+1% Tween 20 (TBS-T). Secondary antibody, goat-anti-mouse IgG-AP light chain specific (Southern Biotechnology Associates, Birmingham Ala.), was diluted 1:1000 in blocking buffer, and 100 µl well is reacted for 1 hr at 37° C. Plates are developed with phosphatase substrate (Sigma, St. Louis, Mo.) at room temperature and readings are taken at 15 and 30 minutes. SZP reactive supernatants are further characterized as described in examples 3 through 9.

Example 15

Measurement of SZP in Human Synovial Fluid

An ELISA assay was developed to measure the concentration of SZP in synovial fluids. Anti-human SZP monoclonal antibody was purified from the culture medium of hybridoma cultures, as described above.

Figure 2:
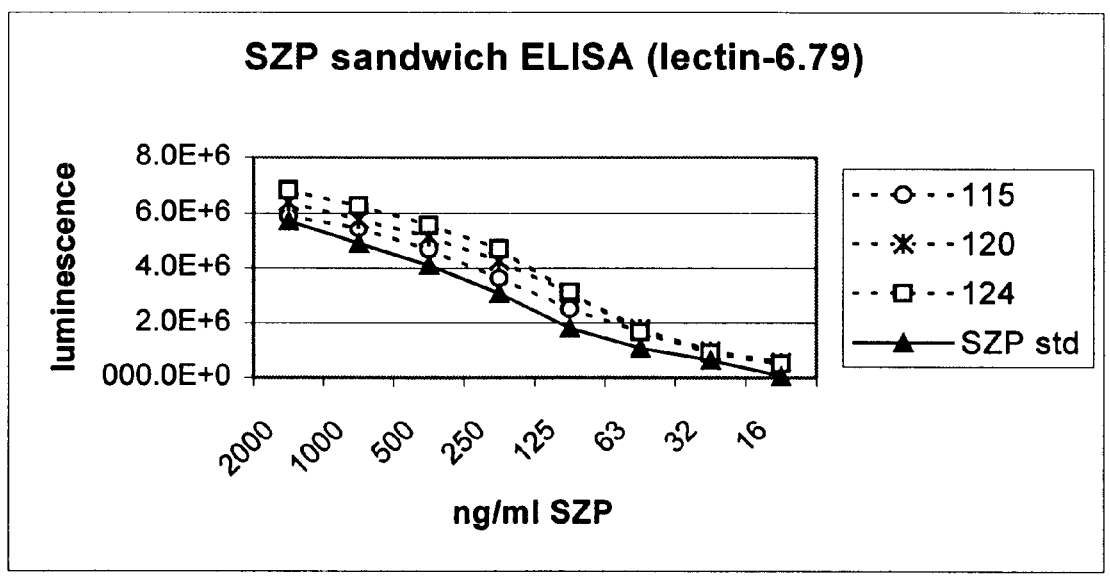
FIG. 2 shows the results of an SZP sandwich ELISA, using lectin-S6.79 MAb, with a SZP standard and three samples of synovial fluids, which are designated samples 115, 120, and 124. The X axis shows the concentration of SZP. The synovial fluids were diluted by two-fold serial dilutions starting with a 1:125 dilution.
Figure 3:
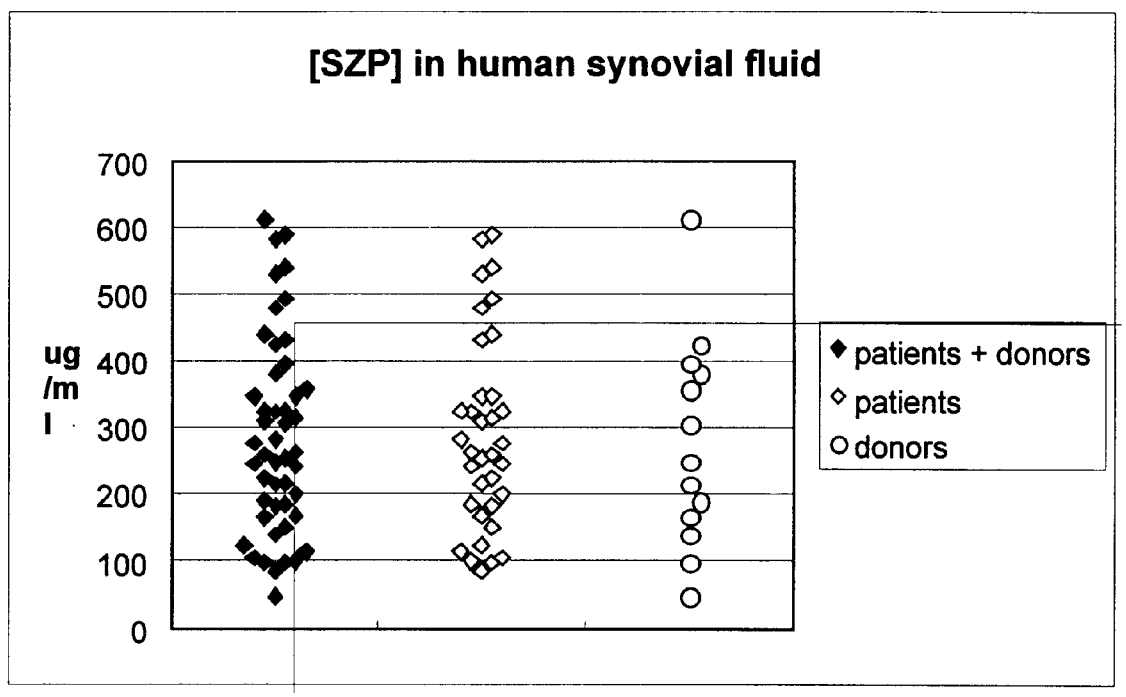
FIG. 3 shows ranges of concentrations of SZP in 50 synovial fluid samples assayed using the SZP sandwich ELISA. The results show the combined data for patients with degenerative joint disease and organ donors and the data for patients and donors separately.

A peanut lectin (Sigma Chemical Co., St. Louis, Mo.) was used to coat black 96-well plates at a concentration of 1 µg/ml in 0.1 M $NaHCO_3$, pH 8.5. Plates were blocked with 1% BSA. Dilutions of synovial fluid or an SZP standard were made and incubated with the lectin-coated plates for 2 h. After washing the plates with PBS-Tween (0.05%), the plates were incubated with an anti-SZP monoclonal antibody for 1 h, washed and incubated with a goat-anti-mouse-HRP conjugate (Pierce Chemical Co., Rockford, Ill.). Bound HRP enzyme activity was detected with a chemiluminescent substrate (Pierce Chemical Co, Rockford, Ill.) and a luminometer. Two-fold serial dilutions (1:60 to 1:4000) were sufficient to measure the concentrations of SZP in synovial fluid. The assay was able to measure an SZP concentration in the range of 25–5000 ng/ml. See FIG. 2. Fifty samples of human synovial fluids from organ donors or patients with degenerative joint disease contained a range of SZP concentration from about 60–600 µg/ml. The mean value was 286 µg/ml with a standard deviation of 146 µg/ml. The data are shown in FIG. 3.

Similar results were obtained using SDS-PAGE analysis. The concentration of SZP in human synovial fluid was also assessed using Western blotting of two-fold dilutions of synovial fluid compared to a purified SZP standard. Equivalent amounts of SZP were separated by SDS-PAGE and transferred to nitrocellulose, then serial dilutions of synovial fluid were compared to purified SZP to determine the relative detection limits for both preparations. Such an experiment showed synovial fluid to have about ten times the amount of SZP as the purified SZP stock solution with a concentration of 20 µg/ml. This experiment also estimated the concentration of SZP in synovial fluid to be about 200 µg/ml.

Example 16

Cross-reactivity of Antibodies to Bovine, Guinea Pig, and Rabbit SZPs

Synovial fluid was collected from various species including bovine, dog, guinea pig and rabbit for Western analysis. MAb S6.79 showed strong cross-reactivity against proteins at approximately 330–350 kDa in dog and rabbit samples, their staining intensity at 1 µl per sample is close to that of 0.25 µl of human synovial fluid. MAb S6.79 also reacted with bovine and guinea pig synovial fluids, but the staining intensity was weaker. Furthermore, in guinea pig the immunoreactive bands are smaller in size, at approximately 250 kDa molecular weight. To confirm that the immunostained bands detected by S6.79 are indeed SZP, an antibody absorption experiment was performed. MAb S6.79 was pre-incubated with either BSA or purified SZP (1:25 ratio in weight) before applying to the synovial fluid-containing blot. Pre-incubation of antibody with BSA did not change or reduce the staining pattern or intensity of immunostained bands. As expected, pre-incubation of antibody with purified SZP almost completely abolished the staining. These data clearly indicated that the immunostained bands were SZP.

Throughout this application, various publications are referenced. The disclosures of these publications in their entireties are hereby incorporated by reference into this application in order to describe more fully the state of the art to which this invention pertains.

Although the present process has been described with reference to specific details of certain embodiments thereof, it is not intended that such details should be regarded as limitations upon the scope of the invention except as and to the extent that they are included in the accompanying claims.

REFERENCES

1. Abrahmsen L et al. (1991) Engineering subtilisin and its substrates for efficient ligation of peptide bonds in aqueous solution. Biochemistry 30:4151–9.
2. Amersham Life Science (1995) Proximity News. Issue 17.
3. Amersham Life Science (1995) Proximity News. Issue 18.
4. Aydelotte M B and Kuettner K E (1988) Differences between sub-populations of cultured bovine articular chondrocytes. I. Morphology and cartilage matrix production. Connect Tissue Res. 18:205–222.
5. Aydelotte M B et al. (1988) Differences between sub-populations of cultured bovine articular chondrocytes. II. Proteoglycan metabolism. Connect Tissue Res 18:223–234.
6. Baggiolini M et al. (1992) Interleukin-8, a chemotactic and inflammatory cytokine. FEBS Lett. 307:97–101.
7. Bicamumpaka C et al. (1998) Development of a fluorescence polarization immunoassay (FPIA) for the quantitative determination of paclitaxel. J. Immunol. Methods 212:1–7.
8. Bodansky M. and Trost B., Ed., "Principles of Peptide Synthesis" Springer-Verlag Inc., N.Y. (1993).
9. Boerner P et al. (1991) Production of antigen-specific human monoclonal antibodies from in vitro-primed human splenocytes. J. Immunol. 147:86–95.
10. Brodeur et al., "Monoclonal Antibody Production Techniques and Applications" Marcel Dekker, Inc., New York, (1987) pp. 51–63.
11. Bruggemann M. et al. (1993) Designer mice: the production of human antibody repertoires in transgenic animals. Year Immunol. 1993;7:33–40.
12. Carter P et al. (1992) Humanization of an anti-p185HER2 antibody for human cancer therapy. Proc. Natl. Acad. Sci. U S A. 89:4285–89.
13. Chothia C et al. (1987) Canonical structures for the hypervariable regions of immunoglobulins. J. Mol. Biol. 196:901–17.
14. Clark-Lewis I et al. (1994) Structural requirements for interleukin-8 function identified by design of analogs and CXC chemokine hybrids. J. Biol. Chem. 269:16075–81.
15. Clark-Lewis I et al. (1991) Chemical synthesis, purification, and characterization of two inflammatory proteins, neutrophil activating peptide 1 (interleukin-8) and neutrophil activating peptide. Biochemistry 30:3128–35.
16. Cote et al. (1985), Monoclonal Antibodies and Cancer Therapy, Alan R. Liss, p. 77.
17. Dawson P E et al. (1994) Synthesis of proteins by native chemical ligation. Science 266:776–79.
18. deLisle Milton R C et al. (1992) "Techniques in Protein Chemistry IV" Academic Press, New York, pp. 257–267.
19. Edwards P R, Leatherbarrow R J. Determination of association rate constants by an optical biosensor using initial rate analysis. Anal Biochem. 1997; 246:1–6.

20. Eisenbraun M D, et al. Examination of parameters affecting the elicitation of humoral immune response by particle bombardment mediated genetic immunization. DNA Cell Biol. 1993;12:791–797.
21. Fägerstam L G et al (1992) Biospecific interaction analysis using surface plasmon resonance detection applied to kinetic, binding site and concentration analysis. Chromatography 1992;597:397–410.
22. Flannery C R et al. (1999) Articular cartilage superficial zone protein (SZP) is homologous to megakaryocyte stimulating factor precursor and is a multifunctional proteoglycan with potential growth-promoting, cytoprotective, and lubricating properties in cartilage metabolism. Biochem Biophys Res Commun. 254(3):535–41.
23. Goding, "Monoclonal Antibodies: Principles and Practice" Academic Press, (1986) pp. 59–103).
24. Grant, G. A., "Synthetic Peptides: A User Guide" W.H. Freeman and Co., N.Y. (1992).
25. Handbook of Monoclonal Antibodies, Ferrone et al., eds., Noges Publications, Park Ridge, N.J., (1985) ch. 22 and pp. 303–357.
26. Harlow and Lane "Antibodies, A Laboratory Manual" Cold Spring Harbor Publications, New York, (1988).
27. Hoogenboom H R et al. (1992) By-passing immunisation. Human antibodies from synthetic repertoires of germline VH gene segments rearranged in vitro. J Mol Biol. 227:381–88.
28. Jakobovits A et al. (1993) Analysis of homozygous mutant chimeric mice: deletion of the immunoglobulin heavy-chain joining region blocks B-cell development and antibody production. Proc Natl Acad Sci U S A. 90:2551–55.
29. Jakobovits A et al. (1993) Germ-line transmission and expression of a human-derived yeast artificial chromosome. Nature. 362:255–58.
30. Jiskoot W et al (1991) Preparation and application of a fluorescein-labeled peptide for determining the affinity constant of a monoclonal antibody-hapten complex by fluorescence polarization. Anal Biochem. 196:421–26.
31. Jolley M E (1981) Fluorescence polarization immunoassay for the determination of therapeutic drug levels in human plasma. J Anal Toxicol. 5:236–40.
32. Jones P T et al. (1986) Replacing the complementarity-determining regions in a human antibody with those from a mouse. Nature 321:522–25.
33. Kabat E A et al. (1987) "Sequences of Proteins of Immunological Interest" National Institutes of Health, Bethesda, Md.
34. Kaplan J B, et al. (1997) Characterization of a soluble vascular endothelial growth factor receptor-immunoglobulin chimera. Growth Factors 14:243–256.
35. Khaw B A et al. (1980) Myocardial infarct imaging of antibodies to canine cardiac myosin with indium-111-diethylenetriamine pentaacetic acid. Science 209:295–97.
36. Kilpatrick K E et al. (1997) Rapid development of affinity matured monoclonal antibodies using RIMMS. Hybridoma 16:381–89.
37. Kilpatrick K E, et al. (1998) Gene gun delivered DNA-based immunizations mediate rapid production of murine monoclonal antibodies to the Flt-3 receptor. Hybridoma 17:569–576.
38. Kohler G. et al. (1975) Continuous cultures of fused cells secreting antibody of predefined specificity. Nature 256:495–7.
39. Kozbor D (1984) A human hybrid myeloma for production of human monoclonal antibodies. J. Immunol. 133:3001–5.
40. Krejcarek G E et al. (1977) Covalent attachment of chelating groups to macromolecules. Biochem. Biophys. Res. Commun. 77:581–85.
41. Lindley K M et al. (2000) Production of Monoclonal Antibodies Using Recombinant Baculovirus Displaying gp64-Fusion Proteins. J. Immunological Methods 2000;234:123–135.
42. Marcelino J et al. (1999) CACP, encoding a secreted proteoglycan, is mutated in camptodactyl-arthropathy-coxa vara-pericarditis syndrome. Nature Genetics 23:319–322.
43. Marks J D et al. (1991) By-passing immunization. Human antibodies from V-gene libraries displayed on phage. J. Mol. Biol. 222:581–97.
44. Merberg et al. (1993) A Comparison of Vitronectin and Megakaryocyte Stimulaing Factor. In: Biology of Vitronectins and Their Receptors (eds. Pressner et al.), pp. 45–53.
45. Morrison L E (1988) Time-resolved detection of energy transfer:theory and application to immunoassays. Anal. Biochem. 174:101–120.
46. Morrison S L et al. (1984) Chimeric human antibody molecules: mouse antigen-binding domains with human constant region domains. Proc. Natl. Acad. Sci. USA, 81:6851–6855.
47. Munson P J et al. (1980) Ligand: a versatile computerized approach for characterization of ligand-binding systems. Anal Biochem. 107:220–39.
48. O'Reilly, D. R., Miller, L. K., and Luckow, V. A. (1992) "Baculovirus expression vectors: A laboratory manual". Oxford Univ. Press, New York.
49. Park Y-W, Cummings R T, Wu L, Zeng S, Caameron P M, Woodss A, Zaller D M, Marcy A I and Hermes J D: Homogenouse Proximity tyrosine kinasee assays:scintillation proximity assay versus homogenous time-resolved fluorescence. Anal. Biochem. 1999;269:94–104.
50. Pertmer T M, et al. Influenza virus nucleo-protein-specific immunoglobulin G subclasses and cytokine response elicited by DNA vaccination are dependent on the route of vector DNA delivery. J. Virol 1996;70:6119–6125.
51. Presta L G (1992) Antibody engineering. Curr. Opin. Biotechnol. 3:394–98.
52. Presta L G et al. (1993) Humanization of an antibody directed against IgE. J Immunol. 151:2623–32.
53. Rajarathnam, K. et al. (1994) 1H NMR studies of interleukin 8 analogs: characterization of the domains essential for function. Biochemistry 33:6623–30.
54. Riechmann L et al. (1988) Reshaping human antibodies for therapy. Nature 332:323–27.
55. Sambrook, J., Fritsch, E. F., and Maniatis, T., (1989) "Molecular Cloning: A laboratory manual". Cold Spring Harbor Lab. Press, Plainview, N.Y.
56. Schmid T M et al. (1994) Immunohistochemical distribution of a novel proteoglycan in the surface lamina of articular cartilage. Proceedings of the Orthopedic Research Society, p. 97–17.
57. Schnolzer, M et al. (1992) Constructing proteins by dovetailing unprotected synthetic peptides: backbone-engineered HIV protease. Science 256:221–5.
58. Schumacher B L et al. (1994) A novel proteoglycan synthesized and secreted by chondrocytes of the superficial zone of articular cartilage. Arch. Biochem. Biophys. 311:144–52.
59. Schumacher B L et al. (1999) Immunodetection and partial cDNA sequence of the proteoglycan, superficial zone protein, synthesized by cells lining synovial joints. J. Orthop. Res.17:110–120.

60. Seethala R and Menzel R (1998) A fluorescence polarization competition immunoassay for tyrosine kinases. Anal. Biochem. 255:257–62.
61. Sims et al. (1993) A humanized CD18 antibody can block function without cell destruction. J. Immunol.151:2296–308.
62. Smith et al., Antibodies in Human Diagnosis and Therapy, Haber et al., eds., Raven Press, New York (1977) pp. 365–389.
63. Stenroos k, Hurskaainen P, Eriksson S, Hemmila I, Blomberg K and Linddqvist (1988) Homogeneous rime-resolved IL-2-IL-2RRα Assay using fluorescence resonance energy transfer. Cytokine 1100(7):495–499.
64. Su J-L et al. (1999) Use of a PPAR gamma-specific monoclonal antibody to demonstrate thiazolidinediones induce PPAR gamma receptor expression in vitro. Hybridoma 18:273–280.
65. Su J-L, Kilpatrick K E, Champion B R, Morris D C, Lehmann J M and Kost A T: Fluorescent microtiter screening assay for immunocytochemically reactive antibodies. BioTechniques 1997;22:320–324.
66. Su J-L, Becherer D, Edwards C, Burkhart W, McGeehan G M and Champion B R (1995) Monoclonal antibodies against human collagenase and stromelysin. Hybridoma 14:383–390.
67. Su J-L, Simmons C. J., Wisely B. Ellis B. and Winegar D. A. (1998) Monitoring of PPAR alpha protein expression in human tissue by the use of PPAR alpha-specific MAbs. Hybridoma. 17:47–53.
68. Verhoeyen M. et al. (1988) Reshaping human antibodies: grafting an antilysozyme activity. Science, 239:1534–1536.
69. Zoller, M. J. et al. (1982) Oligonucleotide-directed mutagenesis using M13-derived vectors:An efficient and general procedure for the production of point mutations in any fragment of DNA. Nucl. Acids Res. 10:6487–500.

What is claimed is:

1. A monoclonal antibody or fragment thereof having specific binding affinity for human superficial zone protein and specific binding affinity for bovine superficial protein, wherein the binding affinity of the antibody or fragment thereof for human superficial zone protein is the same or greater than the binding affinity for bovine superficial zone protein in a competitive binding assay, resonant mirror biosensor analysis, or surface plasmon resonance analysis.

2. The antibody or fragment thereof of claim 1, wherein the antibody or fragment thereof binds a glycosylated or non-glycosylated superficial zone protein.

3. The antibody or fragment thereof of claim 1, wherein the antibody or fragment thereof binds non-reduced superficial zone protein.

4. The antibody or fragment thereof of claim 1, wherein the antibody or fragment thereof binds reduced and non-reduced superficial zone protein.

5. The antibody or fragment thereof of claim 2, wherein the antibody or fragment thereof binds human superficial zone protein and superficial zone protein from at least one non-human species.

6. The antibody or fragment thereof of claim 1, wherein the antibody or fragment thereof binds superficial zone protein from at least one non-human species selected from the group consisting of dog, guinea pig, and rabbit.

7. The antibody of claim 1, wherein the antibody is an intact antibody.

8. The antibody fragment of claim 1, wherein the fragment is an F(ab) or F(ab')$_2$ fragment.

9. An antibody reagent kit comprising containers of the antibody or fragment thereof of claim 1 and reagents for detecting binding of the antibody or fragment thereof to a protein, protein core or protein fragment.

10. A hybridoma cell that produces the antibody of claim 1.

* * * * *

UNITED STATES PATENT AND TRADEMARK OFFICE
CERTIFICATE OF CORRECTION

PATENT NO. : 6,720,156 B2
DATED : April 13, 2004
INVENTOR(S) : Jeff T. Hutchins et al.

It is certified that error appears in the above-identified patent and that said Letters Patent is hereby corrected as shown below:

Column 41,
Line 64, "claim 2" should read -- claim 1 --.

Signed and Sealed this

Twenty-seventh Day of September, 2005

JON W. DUDAS
*Director of the United States Patent and Trademark Office*

```
                         SEQUENCE LISTING

<160> NUMBER OF SEQ ID NOS: 7

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence:/note=
      synthetic construct

<400> SEQUENCE: 1

Arg Gly Gly Ser Ile Gln Gln Tyr Ile Tyr
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence:/note=
      synthetic construct

<400> SEQUENCE: 2

Asp Gln Tyr Tyr Asn Ile Asp Val Pro Ser
1               5                   10

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence:/note=
      synthetic construct

<400> SEQUENCE: 3

Gly Phe Gly Gly Leu Thr Gly Gln Ile Val Ala Ala Leu Ser Thr Ala
1               5                   10                  15

Lys

<210> SEQ ID NO 4
<211> LENGTH: 8
<212> TYPE: PRT
<213> ORGANISM: Artificial Sequence
<220> FEATURE:
```

-continued

```
<223> OTHER INFORMATION: Description of Artificial Sequence:/note=
      synthetic construct

<400> SEQUENCE: 4

Glu Thr Ser Leu Thr Val Asn Lys
 1               5

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence:/note=
      synthetic construct

<400> SEQUENCE: 5

Glu Thr Ser Leu Thr Val Asn Lys Glu Thr Thr Val Glu Thr Lys
 1               5                  10                  15

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence:/note=
      synthetic construct

<400> SEQUENCE: 6

Asp Gln Tyr Tyr Asn Ile Asp Val Pro Ser Arg
 1               5                  10

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence:/note=
      synthetic construct

<400> SEQUENCE: 7

Cys Phe Glu Ser Phe Glu Arg
 1               5
```